(12) United States Patent
Liu et al.

(10) Patent No.: US 7,947,821 B2
(45) Date of Patent: May 24, 2011

(54) OPTIMIZED DNA SEQUENCES ENCODING RECOMBINANT HUMAN BONE MORPHOGENETIC PROTEIN-2 (RHBMP-2), PREPARATION METHOD AND THE USES THEREOF

(75) Inventors: Changshen Liu, Shanghai (CN); Jun Lin, Shanghai (CN); Jiangchao Qian, Shanghai (CN); Yuan Yuan, Shanghai (CN)

(73) Assignee: Shanghai Rebone Biomaterials Co., Ltd., Shanghai (CN)

( * ) Notice: Subject to any disclaimer, the term of this patent is extended or adjusted under 35 U.S.C. 154(b) by 0 days.

(21) Appl. No.: 12/623,527

(22) Filed: Nov. 23, 2009

(65) Prior Publication Data
US 2010/0190209 A1 Jul. 29, 2010

(30) Foreign Application Priority Data

Jan. 23, 2009 (CN) .......................... 2009 1 0045832

(51) Int. Cl.
| | |
|---|---|
| C07H 21/02 | (2006.01) |
| C07H 21/04 | (2006.01) |
| C12N 15/63 | (2006.01) |
| C12N 15/85 | (2006.01) |
| C12N 15/86 | (2006.01) |
| C12N 1/20 | (2006.01) |

(52) U.S. Cl. ................... 536/23.1; 536/23.5; 435/320.1; 435/325; 435/252.1

(58) Field of Classification Search ........................ None
See application file for complete search history.

(56) References Cited

OTHER PUBLICATIONS

Ihm et al. (Soluble expression and purification of synthetic human bone morphogenetic protein-2 in *Escherichia coli*, Journal of Biochemistry and Molecular Biology, vol. 41, Issue 5, p. 404-407, 2008).*
Baneyx, "Recombinant protein expression in *Escherichia coli*", Current Opinion in Biotechnology, 1999, vol. 10, pp. 411-421.
Wu et al., "The Synthetic Gene Designer: A Flexible web platform to explore sequence manipulation for heterologous expression", Protein Expression and Purification 2006, vol. 47, No. 2, pp. 441-445.
Kane, "Effects of rare codon clusters on high-level expression of heterologous proteins in *Escherichia coli*". Current Opinion in Biotechnology, 1995, vol. 6, pp. 494-500.
Sorenson et al., "Codon Usage Determines Translation Rate in *Escherichia coli*", Journal of Molecular Biology, 1989, vol. 207, No. 2, pp. 365-377.
Zhang et al., "Low-usage codons in *Escherichia coli*, yeast, fruit fly and primates", Gene, 1991, vol. 105, No. 1, pp. 61-72.
Comeron et al., "An Evaluation of Measures of Synonymous Codon Usage Bias", Journal of Molecular Evolution, 1998, vol. 47, No. 3, pp. 268-274.
Xu et al., "Design and Implementation of DB Sequence Optimization Software", Chinese Journal of Biotecnology, 2006, vol. 22, No. 6, pp. 1032-1035. (English Abstract provided).
Sasaoka et al., "A prostanoid receptor EP4 agonist enhances ectopic bone formation induced by recombinant human bone morphogenetic protein-2", Biochemical and Biophysical Research Communications, 2004, vol. 318, pp. 704-709.
Grillo, "Tracheal Replacement", Ann. Thorac. Surg., 1990, vol. 49, pp. 864-865.
Urist et al., "Bone Regeneration under the Influence of a Bone Morphogenetic Protein (BMP) Beta Tricalcium Phosphate (TCP) Composite in Skull Trephine Defects in Dogs", Clinical Orthopaedics and RelatedResearch, 1987, No. 214, pp. 295-304.
Sugiura, "Cloning and functional characterization of the 5'-flanking region of the human bone morphogenetic protein-2 gene", Biochem J, 1999, vol. 338, pp. 433-440.
Wozney et al., "Novel Regulators of Bone Formation: Molecular Clones and Activites", Science, 1988, vol. 242, pp. 1528-1534.
Kubler et al., "Inductive properties of recombinant human BMP-2 produced in a bacterial expression system", International Journal of Oral Maxillofacial Surgery, 1998, vol. 27, pp. 305-309.
Ruppert et al., "Human bone morphogenetic protein 2 contains a heparin-binding site which modifies its biological activity", Eur. J. Biochem., 1996, vol. 237, pp. 295-302.
Lin et al., "Expression of C-terminal Segments of Bone Morphogenetic Protein in *E. coli*", Acta Biochimica et Biophysica Sinica, 1996, vol. 28, No. 1. (7 pages) (English Abstract provided).

* cited by examiner

*Primary Examiner* — Suzanne M Noakes
*Assistant Examiner* — Jae W Lee
(74) *Attorney, Agent, or Firm* — Hamre, Schumann, Mueller & Larson, P.C.

(57) ABSTRACT

The invention discloses an optimized DNA sequence of recombinant human bone morphogenetic protein-2 (rhBMP-2) based on the *Escherichia coli* expression system and a method for the preparation of the rhBMP-2. Specifically, the invention provides the optimal DNA sequences suitable for *Escherichia coli* expression system, the methods for efficient preparation of the rhBMP-2, and the related construction of the recombinant bacteria, the expression and purification technologies. Compared with the traditional hBMP-2 gene without optimizing, the rhBMP-2 expression level of the optimized gene in *Escherichia coli* is increased by 50%. Additionally, this invention also provides a method for preparation long chain rhBMP-2 with enhanced renaturation efficiency and yield of purification.

9 Claims, 3 Drawing Sheets

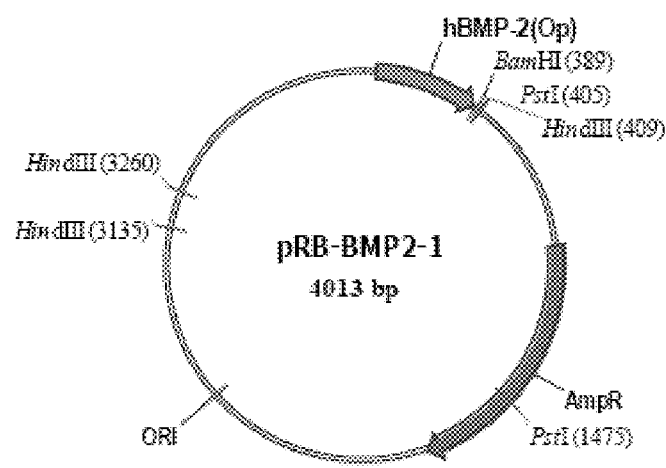
Fig. 1
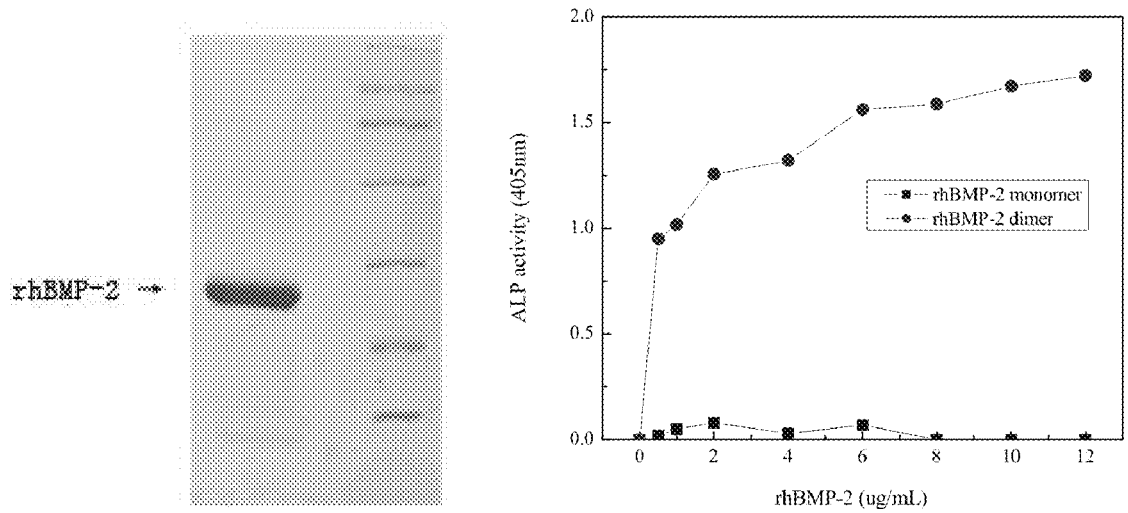
Fig. 2
Fig. 3

SEQUENCE LISTING

<160> NUMBER OF SEQ ID NOS: 8

<210> SEQ ID NO 1
<211> LENGTH: 342
<212> TYPE: DNA
<213> ORGANISM: Homo sapiens
<220> FEATURE:
<221> NAME/KEY: CDS
<222> LOCATION: (1)..(342)

<400> SEQUENCE: 1

```
caa gcc aaa cac aaa cag cgg aaa cgc ctt aag tcc agc tgt aag aga      48
Gln Ala Lys His Lys Gln Arg Lys Arg Leu Lys Ser Ser Cys Lys Arg
  1               5                  10                  15 cac cct ttg tac gtg gac ttc agt gac gtg ggg tgg aat gac tgg att      96
His Pro Leu Tyr Val Asp Phe Ser Asp Val Gly Trp Asn Asp Trp Ile
             20                  25                  30 gtg gct ccc ccg ggg tat cac gcc ttt tac tgc cac gga gaa tgc cct     144
Val Ala Pro Pro Gly Tyr His Ala Phe Tyr Cys His Gly Glu Cys Pro
         35                  40                  45 ttt cct ctg gct gat cat ctg aac tcc act aat cat gcc att gtt cag     192
Phe Pro Leu Ala Asp His Leu Asn Ser Thr Asn His Ala Ile Val Gln
     50                  55                  60 acg ttg gtc aac tct gtt aac tct aag att cct aag gca tgc tgt gtc     240
Thr Leu Val Asn Ser Val Asn Ser Lys Ile Pro Lys Ala Cys Cys Val
 65                  70                  75                  80 ccg aca gaa ctc agt gct atc tcg atg ctg tac ctt gac gag aat gaa     288
Pro Thr Glu Leu Ser Ala Ile Ser Met Leu Tyr Leu Asp Glu Asn Glu
                 85                  90                  95 aag gtt gta tta aag aac tat cag gac atg gtt gtg gag ggt tgt ggg     336
Lys Val Val Leu Lys Asn Tyr Gln Asp Met Val Val Glu Gly Cys Gly
            100                 105                 110 tgt cgt                                                             342
Cys Arg
```

<210> SEQ ID NO 2
<211> LENGTH: 114
<212> TYPE: PRT
<213> ORGANISM: Homo sapiens

<400> SEQUENCE: 2

```
Gln Ala Lys His Lys Gln Arg Lys Arg Leu Lys Ser Ser Cys Lys Arg
  1               5                  10                  15

His Pro Leu Tyr Val Asp Phe Ser Asp Val Gly Trp Asn Asp Trp Ile
             20                  25                  30

Val Ala Pro Pro Gly Tyr His Ala Phe Tyr Cys His Gly Glu Cys Pro
         35                  40                  45

Phe Pro Leu Ala Asp His Leu Asn Ser Thr Asn His Ala Ile Val Gln
     50                  55                  60

Thr Leu Val Asn Ser Val Asn Ser Lys Ile Pro Lys Ala Cys Cys Val
 65                  70                  75                  80

Pro Thr Glu Leu Ser Ala Ile Ser Met Leu Tyr Leu Asp Glu Asn Glu
                 85                  90                  95

Lys Val Val Leu Lys Asn Tyr Gln Asp Met Val Val Glu Gly Cys Gly
            100                 105                 110

Cys Arg
```

<210> SEQ ID NO 3
<211> LENGTH: 342

```
<212> TYPE: DNA
<213> ORGANISM: Artificial
<220> FEATURE:
<223> OTHER INFORMATION: optimized rhBMP-2 coding sequence

<400> SEQUENCE: 3
caggcgaaac ataaacagcg caaacgtctg aaaagcagct gcaaacgcca tccgctgtat      60
gtggatttca gcgatgtggg ctggaacgat tggattgtgg ttccgccggg ctatcatgcg     120
ttttattgcc atggcgaatg cccgtttccg ctggcggatc atctgaacag caccaaccat     180
gcgattgtgc agaccctggt gaacagcgtg aacagcaaaa ttccgaaggc gtgctgcgtg     240
ccgaccgaac tgagcgcgat tagcatgctg tatctggatg aaaacgaaaa agtggtgctg     300
aaaaactatc aggatatggt ggtggaaggt tgcggctgcc gc                        342

<210> SEQ ID NO 4
<211> LENGTH: 342
<212> TYPE: DNA
<213> ORGANISM: Artificial
<220> FEATURE:
<223> OTHER INFORMATION: optimized rhBMP-2 coding sequence

<400> SEQUENCE: 4
caggcgaaac ataaacagcg caaacgcctg aaaagcagct gcaaacgcca tccgctgtat      60 gtggattttta gcgatgtggg ctggaacgat tggattgtgg cgccgccggg ctatcatgcg    120
ttttattgcc atggcgaatg cccgtttccg ctggcggatc atctgaacag caccaaccat     180
gcgattgtgc agaccctggt gaacagcgtg aacagcaaaa ttccgaaagc gtgctgcgtg    240
ccgaccgaac tgagcgcgat tagcatgctg tatctggatg aaaacgaaaa agtggtgctg     300
aaaaactatc aggatatggt ggtggaaggc tgcggctgcc gc                        342

<210> SEQ ID NO 5
<211> LENGTH: 390
<212> TYPE: DNA
<213> ORGANISM: Artificial
<220> FEATURE:
<223> OTHER INFORMATION: long chain rhBMP-2
<220> FEATURE:
<221> NAME/KEY: CDS
<222> LOCATION: (1)..(390)

<400> SEQUENCE: 5 aaa cgt cat gat ggc aaa ggc cat ccg ctg cat aaa cgc gaa aaa cgc        48
Lys Arg His Asp Gly Lys Gly His Pro Leu His Lys Arg Glu Lys Arg
1               5                   10                  15 caa gcc aaa cac aaa cag cgg aaa cgc ctt aag tcc agc tgt aag aga        96
Gln Ala Lys His Lys Gln Arg Lys Arg Leu Lys Ser Ser Cys Lys Arg
            20                  25                  30 cac cct ttg tac gtg gac ttc agt gac gtg ggg tgg aat gac tgg att      144
His Pro Leu Tyr Val Asp Phe Ser Asp Val Gly Trp Asn Asp Trp Ile
        35                  40                  45 gtg gct ccc ccg ggg tat cac gcc ttt tac tgc cac gga gaa tgc cct      192
Val Ala Pro Pro Gly Tyr His Ala Phe Tyr Cys His Gly Glu Cys Pro
    50                  55                  60 ttt cct ctg gct gat cat ctg aac tcc act aat cat gcc att gtt cag      240
Phe Pro Leu Ala Asp His Leu Asn Ser Thr Asn His Ala Ile Val Gln
65                  70                  75                  80 acg ttg gtc aac tct gtt aac tct aag att cct aag gca tgc tgt gtc      288
Thr Leu Val Asn Ser Val Asn Ser Lys Ile Pro Lys Ala Cys Cys Val
                85                  90                  95 ccg aca gaa ctc agt gct atc tcg atg ctg tac ctt gac gag aat gaa      336
Pro Thr Glu Leu Ser Ala Ile Ser Met Leu Tyr Leu Asp Glu Asn Glu
```

```
                       100                 105                 110
aag gtt gta tta aag aac tat cag gac atg gtt gtg gag ggt tgt ggg    384
Lys Val Val Leu Lys Asn Tyr Gln Asp Met Val Val Glu Gly Cys Gly
        115                 120                 125 tgt cgt                                                            390
Cys Arg
    130

<210> SEQ ID NO 6
<211> LENGTH: 130
<212> TYPE: PRT
<213> ORGANISM: Artificial
<220> FEATURE:
<223> OTHER INFORMATION: Synthetic Construct

<400> SEQUENCE: 6

Lys Arg His Asp Gly Lys Gly His Pro Leu His Lys Arg Glu Lys Arg
1               5                   10                  15

Gln Ala Lys His Lys Gln Arg Lys Arg Leu Lys Ser Ser Cys Lys Arg
            20                  25                  30

His Pro Leu Tyr Val Asp Phe Ser Asp Val Gly Trp Asn Asp Trp Ile
        35                  40                  45

Val Ala Pro Pro Gly Tyr His Ala Phe Tyr Cys His Gly Glu Cys Pro
    50                  55                  60

Phe Pro Leu Ala Asp His Leu Asn Ser Thr Asn His Ala Ile Val Gln
65                  70                  75                  80

Thr Leu Val Asn Ser Val Asn Ser Lys Ile Pro Lys Ala Cys Cys Val
                85                  90                  95

Pro Thr Glu Leu Ser Ala Ile Ser Met Leu Tyr Leu Asp Glu Asn Glu
            100                 105                 110

Lys Val Val Leu Lys Asn Tyr Gln Asp Met Val Val Glu Gly Cys Gly
        115                 120                 125

Cys Arg
    130

<210> SEQ ID NO 7
<211> LENGTH: 390
<212> TYPE: DNA
<213> ORGANISM: Artificial
<220> FEATURE:
<223> OTHER INFORMATION: optimized long chain rhBMP-2 coding sequence

<400> SEQUENCE: 7
aaacgtcatg atggcaaagg ccatccgctg cataaacgcg aaaaacgcca ggcgaaacat     60
aaacagcgca aacgcctgaa aagcagctgc aaacgccatc cgctgtatgt ggattttagc    120
gatgtgggct ggaacgattg gattgtggcg ccgccgggct atcatgcgtt ttattgccat    180
ggcgaatgcc cgtttccgct ggcggatcat ctgaacagca ccaaccatgc gattgtgcag    240
accctggtga cagcgtgaa cagcaaaatt ccgaaagcgt gctgcgtgcc gaccgaactg    300
agcgcgatta gcatgctgta tctggatgaa aacgaaaaag tggtgctgaa aaactatcag    360
gatatggtgg tggaaggctg cggctgccgc                                     390

<210> SEQ ID NO 8
<211> LENGTH: 390
<212> TYPE: DNA
<213> ORGANISM: Artificial
<220> FEATURE:
<223> OTHER INFORMATION: optimized long chain rhBMP-2 coding sequence

<400> SEQUENCE: 8
```

```
aaacgtcatg atggcaaagg ccatccgctg cataaacgcg aaaaacgcca ggcgaaacat      60
aaacagcgca aacgtctgaa aagcagctgc aaacgccatc cgctgtatgt ggatttcagc     120
gatgtgggct ggaacgattg gattgtggtt ccgccgggct atcatgcgtt ttattgccat     180
ggcgaatgcc cgtttccgct ggcggatcat ctgaacagca ccaaccatgc gattgtgcag     240
accctggtga acagcgtgaa cagcaaaatt ccgaaggcgt gctgcgtgcc gaccgaactg     300
agcgcgatta gcatgctgta tctggatgaa aacgaaaaag tggtgctgaa aaactatcag     360
gatatggtgg tggaaggttg cggctgccgc                                      390
```

OPTIMIZED DNA SEQUENCES ENCODING RECOMBINANT HUMAN BONE MORPHOGENETIC PROTEIN-2 (RHBMP-2), PREPARATION METHOD AND THE USES THEREOF

FIELD OF THE INVENTION

The invention relates to genetic engineering. Specifically, the invention relates to optimized DNA sequences of recombinant human bone morphogenetic protein-2 (rhBMP-2) based on *Escherichia coli* expression system, a method for efficient preparing of the rhBMP-2, and the construction of the related engineered cells, the expression and purification of rhBMP-2.

BACKGROUND OF THE INVENTION

Bone repair associated with fracture delayed union, bone nonunion and bone defect is one of the pending matters in the orthopedics field. For a long time, autogenous bone transplanting, allogeneic bone transplanting and related biomaterials have been applied for bone defect repair. However, for the autogenous bone transplantation, not only the bone source is greatly limited, but also at least 10% clinic complications may follow the bone operation. Furthermore, it requires long-time crawl replacing process after implantation. For the allogeneic bone implantation, there exists great immunity rejection and potential danger of disease dissemination. So, in the past few years, biomaterials and the biomedical products with special functions, therefore, have attracted close attention and have already been used in clinic. However, some reports indicate that the bioactivity and biodegradation of the traditional biomaterials cannot meet the clinic requirement and the therapeutic efficacies are not very good. These drawbacks greatly limit the wide application of biomaterials in clinic.

Bone Morphogenetic Protein (BMP), a kind of multi-functional morphogenesis factor with prominent biological activity in bone growth and repair, has provided new strategy for the therapy of bone nonunion and defects. As early as in 1965, Urist, an American doctor discovered that some substances could induce ectopic bone formation in the decalcifying bone matrix, and named them as bone morphogenetic protein or BMP. To date, over 20 BMP family members have been isolated and characterized, classified as BMP-1, BMP-2 . . . and so on. BMPs (excluding BMP-1) belong to transforming growth factor-beta (TGF-β) superfamily. BMPs not only exert the regulation of various organs growth and cell oriented differentiation in early embryonic tissue patterning phase, but also induce mesenchymal stem cells within organisms irreversibly to cartilage and osteoblast after procreation, thereby playing an important role in bone and tooth formation as well as wound healing. During the concrescence process, the expressing levels of BMPs in the pathological site significantly increase and the BMPs are confined to fracture callus domain. BMP implanted into the soft tissue can induce new ectopic bone, which has already been used as evidence to investigate the bioactivity of BMP. So, BMP possesses the potential of gigantic fundamental research value and wide clinical application.

Among all growth factors, BMP-2 is proven to be the most effective for the bone forming. Up to date, the structure and function of BMP-2 have been deeply addressed. The natural BMP-2, as a non-collagen acid glycoprotein, is hydrophobic, insoluble in water, and easy to dissolve in high concentration urea and guanidinium hydrochloride. Because of the insolubility, it is difficult to be extracted from natural resource or be purified when expressed as the recombinant protein. In addition, BMP-2 molecule has a hydrophobic core and 30% acidic amino acids, so the pI thereof is about 5.0. It is well-established that the three pairs of intrachain disulfide bond and one pair of interchain disulfide bond derived from the seven conserved cysteines residues in the primary structure are critical for maintaining the natural active conformation of BMP-2. If the disulfide bonds in the BMP-2 molecule are reduced, the bioactivity will disappear completely. The mature BMP-2 molecule is in the form of dimmer which is consisted of 2 monomers linked by disulfide bond. Each monomer is composed of 114 amino acids, contains glycosylation site and molecular weight thereof is about 13 KD.

Sampath et al. had analyzed the structure of an osteoinductive protein extracted from ox bone matrix directly and found that even after deglycosylation, the dimer composed of 16 KD and 14 KD polypeptides still has the bioactivity to induce bone forming, indicating that glycosylation is not essential for its activity. That is to say, it is possible to adopt prokaryotic expression system to prepare BMP-2.

In vivo, the precursor of BMP-2 is synthesized with larger molecular weight, composed of signal peptides and carboxyl terminus (C-terminus) including 100-125 amino acids. There are 7 conservative cysteine residues at the C-terminus of BMP-2 molecule, which play an important role in the formation of dimer. After the C-terminus is splitted and released, 2 monomers combine with each other via disulfide bond to form dimer and then the active syn-chain or iso-chain dimmers are secreted. BMP-2 precursor does not have any latent organism recognition sequence Arg-Gly-Asp, which exists in precursor sequence of TGF-β1 and TGF-β2. The N-terminus of the mature peptide is rich in basic amino acids, making BMP-2 precursor easily adhere on extracellular matrix and the biological half-life of the BMP-2 is prolonged. Consequently, the bioactivity of bone formation or signal gradient of hBMP-2 in stage of development and differentiation are enhanced. [Biochem Biophys Res Commun, 2004; 318(3): 704].

BMP-2 can be purified from animal tissue (p-BMP-2) or expressed as recombinant protein (rhBMP-2). As early as in 1979, Urist et al [UAnn Thorac Surg, 1990; 49 (6):864-5] first dissociated and purified BMP-2 from rabbit decalcified bone successfully, extracted the ox bones morphogenesis protein (bBMP) in 1982 from the ox bones, and in 1987, Urist [Clin Orthop Relat Res., 1987 (214):295-304] established a set of standard procedures to extract BMP from human and ox bones. At present, most of p-BMP-2s are obtained from the normal bones of animals, such as ox, pig, sheep, horse, rabbit, mouse and so on. Although BMP widely exists in various animal bone tissues, the content thereof is very tiny, only several micrograms BMP in 1 kilogram of wet weight fresh bone. And for the BMPs from different sources, there are major differences in physicochemical property and molecular structure, as well as in activity for inducing bone-formation and stability. Also, since various BMPs combine with the insoluble non-collagenous protein (iNCP) tightly, it is very difficult to obtain unitary BMP. Therefore, extraction of BMP from animal bone is impeded by its complicated process, poor reproducibility, low yield, and low protein purity. Further, the renaturing process is complicated and it is difficult to maintain the protein activity. At the same time, the protein extracted from animals, when applied in the human body, may cause immunological rejection and risk of spreading of pathogen. Therefore, the BMP-2 extracted from animal is difficult to satisfy the demand of experiments and clinical applications.

The method of producing human BMP-2 by recombinant cells, not only can ensure large-scale production, but also can avoid immunological rejection, which has attracted great attention. Since Wozney et al. obtained the BMP-2 gene from ox bones and BMP-2 was expressed successfully in recombinant *Escherichia coli* in 1988, this method has been used to produce mass-production of human BMP-2 (Wozney J M, Rosen V, Celeste A J, et al, Novel regulators of bone formation: molecular clones and activities, Science, 1988; 242(4885):1525-34).

At present, the expression systems used for BMP-2 expression include both eucaryotic and procaryotic ones. Wozney J M (Wozney J M, Overview of bone morphogenetic proteins, Spine. 2002, 15; 27 (16 Suppl 1): S2-8) presumed that the recombinant hBMP-2 in COS-1 cells had the ability to induce cartilage but not bone formation. Zhao Ming has expressed recombinant human BMP-2 with inducing bioactivity in the eucaryotic cell COS and CHO. In Genetics Institute, Wozney et al. cloned hBMP-2 from the cDNA library of human U-20s cell and found that the full-length cDNA of BMP-2 had 1587 bp, encoding a 396 aa polypeptide. And the mature peptide of 114 amino acids with activity under the action of protease was obtained [Sugiura T., Biochem J. 1999, 338 (Pt2): 433-40]. US Patent Application No. 118363 revealed that COS, CHO etc. could be used to express rhBMP-2.

In eukaryotic cells, most nascent polypeptides undergo one or more types of posttranslational modification, such as glycosylation and disulfide bond formation, which prepare each molecule for its functional role and/or for folding into its biologically active conformation. From this viewpoint, the eukaryotic cell is the ideal expression system to obtain the recombinant hBMP with high biological activity. In fact, the first approved rhBMP-2 protein with the bioactivity to induce the bone formation in vivo was expressed by eucaryotic cells. It was also found that the cell culture medium of the recombinant cell expressing the BMP-2 gene did not show any activity to induce bone formation. Only after purification, can it show a dosage-dependent bone-forming activity. At present, the Infuse™ as rhBMP-2 Bone Graft produced by Medtromic Sofamor Danek Company using eukaryotic cell as the expression system has already been used for vertebral column coalesce and bone defect repair. Also, the OP-1™ as rhBMP-7 produced in CHO cell by Stryker Biotech Company has already been approved by FDA and has been applied in clinic. Unfortunately, the shortcomings associated with eukaryotic expression system includes low yield, high production cost and so on. As a result, the bulk demand of scientific research and clinic is not satisfied.

Compared with the eukaryotic expression system, gene manipulation in the prokaryotic expression system is relatively easy and the gene expression level is high. Additionally, the prokaryotic cell has cell wall, low nutrition requirement, good toleration to culture circumstance, thus resulting in relatively low production cost and high yield. Although, BMP can not be glycosylated in prokaryotic expression system, and expression products appear mostly in the form of inclusion body. As previously stated, glycosylation is not essential for the biological activity of BMP-2 [J. M. Wozney, Science, 1988, 24 2:15 28-15]. Therefore, prokaryotic expression system is also suitable for the expression and production of BMP.

Kubler N P [Int J oral Maxillofac Surg, 1998, 27:30] and Ruppert R [Eur J Biochem, 1996; 237: 295-302] have successfully expressed integrated mature hBMP-2 in *E. coli*. In China, different mature peptide genes of hBMP-2 with various lengths have been also successfully acquired in *E. coli*, and the ensuing studies indicated that the obtained recombinant hBMP-2 has some level of ectopic bone-formed activity. However, the researches in the world can not go further to carry out repeatable annealing and purify human mature peptide BMP-2 expressed in recombinant *E. coli*, which impede the commercialization of this product.

Lin Song et al. [Acta Biochimica et Biophysica Sinica, 1996, 28(1):8] discovered that the closer the nascent hBMP-2 got to its mature peptide length, the better bone-forming activity it can induce. In CN Patent 01116754.8, recombinant *E. coli* is constructed for the preparation of the truncated rhBMP-2-108 with 108 amino acids encoded by a DNA fragment of 324 bp. Although the invention can be applied to produce rhBMP-2 in industry, short biological half-life, poor in vivo stability and relatively low biological activity in comparison with the full length hBMP-2, restrict its wide application, especially in case of bone fracture delayed union, bone nonunion, and bone defect.

Modification of the protein structure is frequently used to change the amino acid sequences of the natural proteins, construct truncated and long chain type mutants, with the aim of enhancing expression level, protein activity and stability, such as long-chain type IGF-1 (insulin-like growth factors-1) and so on. Previously, the inventors developed a long chain rhBMP-2 to overcome the difficulties of renaturation, separation, low protein activity and instability in vivo, which greatly limited the industrialization of the rhBMP-2. And we have filed the invention entitled "the preparation and application of long chain recombinant human bone morphogenetic protein-2" (CN 1951964). In addition, optimization of DNA sequence according to the codon bias of the host cell is another important strategy to enhance expression level.

In summary, although it has been reported that BMP-2 was produced in both prokaryotic and eukaryotic recombinant cells, the production technology is still not satisfactory. Therefore, there is a great need to develop a new strategy to efficiently produce rhBMP-2 in *E. coli* and a suitable process for industrialization.

SUMMARY OF THE INVENTION

The aim of this invention is to provide an approach to efficiently express and produce rhBMP-2. Another goal of this invention is to provide related encoding sequences of rhBMP-2, vectors, engineered cells and expression and purification technologies of rhBMP-2.

In the first aspect, the invention provides a polynucleotide encoding recombinant human bone morphogenetic protein-2 or rhBMP-2, wherein the polynucleotide encodes the mature polypeptide of rhBMP-2 as shown in SEQ ID NO: 2, and the polynucleotide has the following properties:

in SEQ ID NO: 2, the codon of the $9^{th}$ amino acid is cgc;
in SEQ ID NO: 2, the codon of the $23^{th}$ amino acid is ttt;
in SEQ ID NO: 2, the codon of the $34^{th}$ amino acid is gcg;
in SEQ ID NO: 2, the codon of the $86^{th}$ amino acid is aaa; and
in SEQ ID NO: 2, the codon of the $110^{th}$ amino acid is ggc.

In a preferred embodiment, the expression level of the rhBMP-2 of the polynucleotide in *Escherichia coli* is improved by at least 40%, or 50% in *Escherichia coli*, as compared with the polynucleotide as shown in SEQ ID NO: 1.

In a preferred embodiment, the coding region of mature rhBMP-2 in the polynucleotide is shown in SEQ ID NO: 4.

In a preferred embodiment, the sequence of polynucleotide is shown in SEQ ID NO: 4 or 8.

In the 2nd aspect, the invention provides an expression vector for rhBMP-2 preparation wherein the expression vector contains the polynucleotide of the 1st aspect.

In the 3rd aspect, the invention provides an engineered cell for rhBMP-2 preparation wherein the engineered cell contains the expression vector of the 2nd aspect.

In a preferred embodiment, the engineered cell is *Escherichia coli*.

In the 4th aspect, the invention provides a method for the preparation of rhBMP-2 comprising the following steps:

(a) culturing the engineered cell of the 3rd aspect under suitable expression conditions, thereby secreting the rhBMP-2, wherein the engineered cell is *Escherichia coli*; and (b) separating and purifying the expressed rhBMP-2.

In a preferred embodiment, the step (b) comprises separating, denaturing of the inclusion bodies of rhBMP-2, and renaturing of rhBMP-2 protein, as well as purifying the renatured rhBMP-2.

DESCRIPTION OF DRAWINGS

FIG. 1 shows the optimal genetic expression plasmid pRB-BMP-2-1 (4013 bp) of rhBMP-2.

FIG. 2 shows the electrophoresis of rhBMP-2.

FIG. 3 Comparison of ALP activity of rhBMP-2 monomer and dimmer obtained from the optimized DNA sequence of hBMP-2

DETAILED DESCRIPTION OF INVENTION

Figure 4:
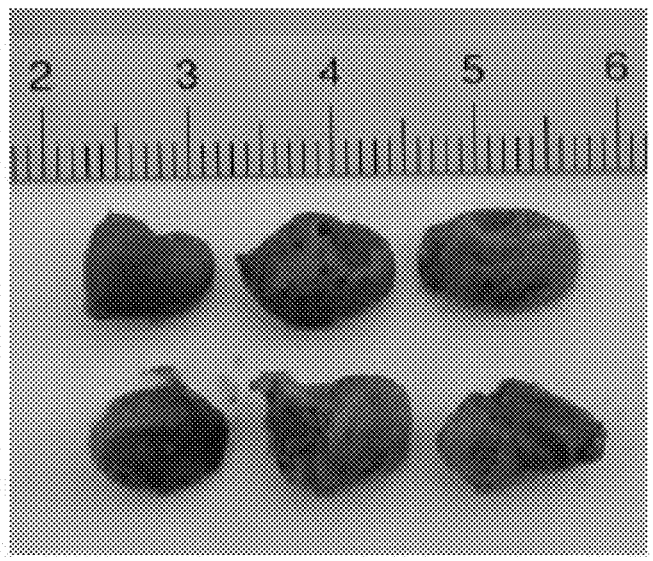
FIG. 4 shows the ectopic fresh bone of rhBMP-2.

After extensive and intensive screen, a lot of hBMP-2 gene sequences, particularly suitable for expression in *E. coli* were selected and applied in this invention.

Genes and proteins of human BMP-2

The cDNA sequence of human BMP-2 mature peptides is shown in SEQ ID NO: 1:

```
                                        (SEQ ID NO: 1)
caa gcc aaa cac aaa cag cgg aaa cgc ctt aag tcc agc tgt aag aga cac cct ttg tac gtg gac ttc agt gac gtg ggg tgg aat gac tgg att gtg gct ccc ccg ggg tat cac gcc ttt tac tgc cac gga gaa tgc cct ttt cct ctg gct gat cat ctg aac tcc act aat cat gcc att gtt cag acg ttg gtc aac tct gtt aac tct aag att cct aag gca tgc tgt gtc ccg aca gaa ctc agt gct atc tcg atg ctg tac ctt gac gag aat gaa aag gtt gta tta aag aac tat cag gac atg gtt gtg gag ggt tgt ggg tgt cgt
```

The corresponding amino acid sequence of mature human BMP-2 is shown in SEQ ID NO: 2:

```
                               (SEQ ID NO: 2, three-letter code)
Gln Ala Lys His Lys Gln Arg Lys Arg Leu Lys Ser Ser Cys Lys Arg His Pro Leu Tyr Val Asp Phe Ser Asp Val Gly Trp Asn Asp Trp Ile Val Ala Pro Pro Gly Tyr His Ala Phe Tyr Cys His Gly Glu Cys Pro Phe Pro Leu Ala Asp His Leu Asn Ser Thr Asn His Ala Ile Val Glu Thr Leu Val Asn Ser Val Asn Ser Lys Ile Pro Lys Ala Cys Cys Val Pro Thr Glu Leu Ser Ala Ile Ser Met Leu Tyr Leu Asp Glu Asn Glu Lys Val Val Leu Lys Asn Tyr Gln Asp Met Val Val Glu Gly Cys Gly Cys Arg
```

```
                         (SEQ ID NO:2 single letter code)
QAKHKQRKRLKSSCKRHPLYVDFSDVGWNDWIVAPPGYHAFYCHGECPFP

LADHLNSTNHAIVQTLVNSVNSKIPKACCVPTELSAISMLYLDENEKVVL

KNYQDMVVEGCGCR
```

The DNA sequence of long chain hBMP-2 is the precursor of its mature peptides, which is shown in SEQ ID NO: 5:

```
                                        (SEQ ID NO: 5)
aaa cgt cat gat ggc aaa ggc cat ccg ctg cat aaa cgc gaa aaa cgc caa gcc aaa cac aaa cag cgg aaa cgc ctt aag tcc agc tgt aag aga cac cct ttg tac gtg gac ttc agt gac gtg ggg tgg aat gac tgg att gtg gct ccc ccg ggg tat cac gcc ttt tac tgc cac gga gaa tgc cct ttt cct ctg gct gat cat ctg aac tcc act aat cat gcc att gtt cag acg ttg gtc aac tct gtt aac tct aag att cct aag gca tgc tgt gtc ccg aca gaa ctc agt gct atc tcg atg ctg tac ctt gac gag aat gaa aag gtt gta tta aag aac tat cag gac atg gtt gtg gag ggt tgt ggg tgt cgt
```

The amino acid sequence of the long chain human BMP-2 is shown in SEQ ID NO: 6, in which the underlined are the additional 16 amino acids in front of the N-terminal of hBMP-2 mature peptides:

```
                               (SEQ ID NO: 6, three-letter code)
Lys Arg His Asp Gly Lys Gly His Pro Leu His Lys Arg Glu Lys Arg Gln Ala Lys His Lys Gln Arg Lys Arg Leu Lys Ser Ser Cys Lys Arg His Pro Leu Tyr Val Asp Phe Ser Asp Val Gly Trp Asn Asp Trp Ile Val Ala Pro Pro Gly Tyr His Ala Phe Tyr Cys His Gly Glu Cys Pro Phe Pro Leu Ala Asp His Leu Asn Ser Thr Asn His Ala Ile Val Glu Thr Leu Val Asn Ser Val Asn Ser Lys Ile Pro Lys Ala Cys Cys Val Pro Thr Glu Leu Ser Ala Ile Ser Met Leu Tyr Leu
```

-continued

Asp Glu Asn Glu Lys Val Val Leu Lys Asn Tyr Gln

Asp Met Val Val Glu Gly Cys Gly Cys Arg (SEQ ID NO: 6, single letter code)
KRHDGKGHPLHKREKRQAKHKQRKRLKSSCKRHPLYVDFSDVGWNDWIVA

PPGYHAFYCHGECPFPLADHLNSTNHAIVQTLVNSVNSKIPKACCVPTEL

SAISMLYLDENEKVVLKNYQDMVVEGCGCR

Optimization of the Gene Coding Sequence

Although there are 64 kinds of genetic code, the overwhelming majority organisms are prone to use a portion of them. Those most frequently used are called major codons, seldom used are called rare or low-usage codons. Actually, for protein synthesis every organism (including *E. coli*, yeasts, mammalian cells, *Pichia*, vegetal cells and insect cells) shows the different pattern of the codon usage. It is proven that in every organism like *E. coli*, yeast, *drosophila*, primates, there are 8 unique rare codons, which were rarely used. And the expressions of recombinant protein might be affected by the codons usage. Therefore, the gene expression can be enhanced by the optimization of codons—substituting optimal codons for the rare codons according to the specific codon bias of the host strain.

Beside codons, other factors can also affect the gene expression, such as mRNA secondary structure at the translation initiation region, the DNA secondary structure, the GC content of the gene, the frameworks of genetic translation initiation and terminator sequences. Taken together, the strategies of optimizing DNA sequence provide huge opportunities for improving expression level of heterologous proteins in *E. coli*.

The Optimization of Nucleotide Sequences of Mature rhBMP-2 Peptides

The invention provides an optimized encoding sequence of rhBMP-2 which is especially suitable to be expressed in *E. coli* system. The sequence was designed according to the codon bias of *E. coli*. The optimized rhBMP-2 encoding sequence is produced by routine genetic engineering or by point mutation of cDNA prepared by PCR.

In one example, on the basis of SEQ ID NO: 1, a novel cDNA sequence was optimized using software according to the frequency of *E. coli* codon usages (SEQ ID NO: 3).

(SEQ ID NO: 3)
cag gcg aaa cat aaa cag cgc aaa cgt ctg aaa agc agc tgc aaa cgc cat ccg ctg tat gtg gat ttc agc gat gtg ggc tgg aac gat tgg att gtg gtt ccg ccg ggc tat cat gcg ttt tat tgc cat ggc gaa tgc ccg ttt ccg ctg gcg gat cat ctg aac agc acc aac cat gcg att gtg cag acc ctg gtg aac agc gtg aac agc aaa att ccg aag gcg tgc tgc gtg ccg acc gaa ctg agc gcg att agc atg ctg tat ctg gat gaa aac gaa aaa gtg gtg ctg aaa aac tat cag aat ata ata gtg gaa ggt tgc ggc tgc cgc Based on the above cDNA sequence (SEQ ID NO:3), an optimal DNA sequence (as shown in SEQ ID NO:4) of rhBMP-2 genes was proposed by further replacement of some nucleotides. The difference between SEQ ID NO:4 and SEQ ID NO:3 are shown as follows:

cag gcg aaa cat aaa cag cgc aaa ~~cgt~~ (the codon of $9^{th}$ amino acid in mature peptide is cgc) ctg aaa agc agc tgc aaa cgc cat ccg ctg tat gtg gat ~~ttc~~ (the codon of 23th amino acid in mature peptide is ttt) agc gat gtg ggc tgg aac gat tgg att gtg ~~gtt~~ (the codon of $34^{th}$ amino acid in mature peptide is gcg) ccg ccg ggc tat cat gcg ttt tat tgc cat ggc gaa tgc ccg ttt ccg ctg gcg gat cat ctg aac agc acc aac cat gcg att gtg cag acc ctg gtg aac agc gtg aac agc aaa att ccg ~~aag~~ (the codon of $86^{th}$ amino acid in mature peptide is aaa) gcg tgc tgc gtg ccg acc gaa ctg agc gcg att agc atg ctg tat ctg gat gaa aac gaa aaa gtg gtg ctg aaa aac tat cag gat atg gtg gtg gaa ~~ggt~~ (the codon of $110^{th}$ amino acid in mature peptide is ggc) tgc ggc tgc cgc The Optimization of the Nucleotide Sequence of Long-Chain hBMP-2

On the basis of the optimized nucleotide sequence of rhBMP-2 mature peptide consisting of 114 peptides (SEQ ID NO:3), the inventors further added 16 amino acid residues (the $1-16^{th}$ in SEQ ID NO: 6) Lys Arg His Asp Gly Lys Gly His Pro Leu His Lys Arg Glu Lys Arg to the N-terminus by adding the corresponding nucleotide sequence (the $1-48^{th}$ SEQ ID NO: 5) AAA CGT CAT GAT GGC AAA GGC CAT CCG CTG CAT AAA CGC GAA AAA CGC and obtained the optimized DNA sequence of long chain rhBMP-2 (SEQ ID NO:7).

Similarly, on the basis of the optimized nucleotide sequence of rhBMP-2 mature peptide consisting of 114 peptides (SEQ ID NO: 4), 16 amino acid residues (the $1-16^{th}$ in SEQ ID NO: 6) Lys Arg His Asp Gly Lys Gly His Pro Leu His Lys Arg Glu Lys Arg were added to the N-terminus of mature peptide of hBMP-2 by adding the corresponding nucleotide sequence (the $1-48^{th}$ in SEQ ID NO: 5) AAA CGT CAT GAT GGC AAA GGC CAT CCG CTG CAT AAA CGC GAA AAA CGC. So the optimized DNA sequence of long chain rhBMP-2 (SEQ ID NO: 8) is obtained.

AAA CGT CAT GAT GGC AAA GGC CAT CCG CTG CAT AAA

CGC GAA AAA CGC cag gcg aaa cat aaa cag cgc aaa cgc ctg aaa agc agc tgc aaa cgc cat ccg ctg tat gtg gat ttt agc gat gtg ggc tgg aac gat tgg att gtg gcg ccg ccg ggc tat cat gcg ttt tat tgc cat ggc gaa tgc ccg ttt ccg ctg gcg gat cat ctg aac agc acc aac cat -continued

```
gcg att gtg cag acc ctg gtg aac agc gtg aac agc aaa att ccg aaa gcg tgc tgc gtg ccg acc gaa ctg agc gcg att agc atg ctg tat ctg gat gaa aac gaa aaa gtg gtg ctg aaa aac tat cag gat atg gtg gtg gaa ggc tgc ggc tgc cgc
```

The Expression Vector, Engineered Bacteria and Fermentation

Special restriction enzyme cleavage sites were introduced into the 5' and 3' end of the optimized genes, and the optimal genes were cloned into expression vectors (e.g., pBV220) by molecular cloning. Then, E. coli was transformed, with the expression vectors and the transformant was picked up (e.g., Amp resistance) to obtain the engineered bacteria expressing rhBMP-2.

After that, the engineered cells were cultured under appropriate conditions. All the culture medium suitable for the growth and expression of E. coli can be used in the present invention.

The optimized culture conditions are as following: a single colony of E. coli containing expression vector is picked from the selective plate and inoculated into the shake flask with LB culture medium containing antibiotics. After 5-12 h culture in air bath shaker (100-300 rpm) at 25-38° C., the fermentation broth is inoculated to LB culture medium at the inoculation ratio of 1:5-15 (v/v %). The engineered bacteria are cultured under the conditions of 25-38° C., 100-300 rpm until the OD value at 600 nm reaches 0.1-1.4. The LB culture medium contains 10 g/l tryptone, 5 g/l yeast extract, 5 g/l NaCl. The antibiotics are ampicillin, phytomycin, kanamycin at the concentrations between 10-100 µg/ml in LB culture medium. Then temperature is raised to 40-42° C. for 4-6 h. At the end of culture, the fermentation broth is centrifuged (7500-10000 rpm) at 4±2° C., and the bacteria are collected.

Preparation and Renaturation of Inclusion Bodies

In this invention, there is no special limitation to the methods and conditions for breaking bacteria, extracting inclusion bodies and renaturation. The common methods for inclusion bodies of rhBMP-2 or others used in this field can be applied. For instance, cell disruption technique comprises of repeatedly freezing and thawing, sonication disruption, high pressure homogenizing.

In one example, the bacteria were collected and mixed with TE solution at the ratio of 1 g:5-15 ml and subsequently lysozyme was added at the ratio of 1 g:0.3-5 mg. And then, bacteria were broken by cell disruption technique, centrifuged under 6000-10000 rpm and collected. After that, washing buffer was added to the bacteria at the ratio of 1 g:20 ml. After 2-4 h stirring, the cell lysis were centrifuged and collected at 4±2° C. Repeat the above washing process. Then, 10 mM Tris (pH 7.5) solution was added for washing. Finally, the precipitate was collected to obtain the inclusion bodies. The said TE solution contains 6 mM Tris and 10 mM EDTA with pH 7.50. The washing solutions are phosphate buffer, urea aqueous solution, Triton and so on. The inclusion body precipitate was dissolved by adding lysis solution at the concentration of 1 g:5-20 ml (inclusion bodies: lysis solution), then stirred to solubilize for 8-12 h at 4±2° C., and centrifuged for 20-30 min at 6000-10000 rpm under 4±2° C. The supernatant was collected, and diluted to protein level at 0.1-1 mg/ml, then mixed with refolding solution to renature for 2-20 d at the ratio of 1:10-100. The said inclusion body lysis solution comprises 6 M Gu-HCl, 8 M urea, 20 mM PBS, 10 mM DTT and so on.

The said refolding solution may comprises, but is not limited to, 20 mM $Na_2HPO_4 \cdot 12H_2O$, 1.5 mM $NaH_2PO_4 \cdot 2H_2O$, 140 mM NaCl, 5 mM EDTA, 1 mM Tathion and so on.

Purification of Protein

After renaturation, the conventional purification processes, such as anion-exchange chromatography, cation-exchange chromatography, and molecular-exclusion chromatography can be applied to recover the active dimer of rhBMP-2.

The Recombinant Protein of rhBMP-2 and its Application

The result of the electrophoresis of the rhBMP-2 protein obtained by this method showed clear single band, and the purity is above 95%.

The bioactivity of rhBMP-2 protein can be evaluated by in vitro cell culture or in vivo implantation. In vivo implantation experiments include ectopic bone formation and in situ bone formation.

For in vitro cell culture, C2C12 cell, which is myoblast cell, is used for the test of the bioactivity of BMP-2. Since BMP-2 can induce mesenchymal stem cells within organisms irreversibly to cartilage and osteoblast, which show the activity of ALP (alkaline phosphatase). The results indicated that the ALP activity of rhBMP-2 dimer was 9-fold higher than that of the control group (rhBMP-2 monomer).

The rhBMP-2 obtained by the method of the invention was implanted to leg muscle of Kunming mouse. The dose- and time-dependent effect of the rhBMP-2 on the ectopic bone formation activity was evaluated by the amount of the bone formed. The results indicated that the amount of ectopic bone formation increased with the increasing of the dosage and time, a typical dosage- and time-dependent manner. In contrast, no new bone formation can be observed in control group (without rhBMP-2).

The rhBMP-2 prepared in this invention was implanted to radius segment defection with the length of 1.5 cm in New Zealand rabbits. New bone formation, bone density, osteotylus formation, bone knitting in defection domain were all examined and compared. The results demonstrated that the rhBMP-2 showed excellent in-situ osteoinductive activity. After 12 weeks implantation, 1.5 cm radius defection could be filled with new bone matrix completely, and almost recovered to normal morphology, and formed normal cortical bone.

The results of implantation experiments above demonstrated that the protein obtained in this invention had high osteoinductive activity, and can be applied separately or in combination with other carriers.

The rhBMP-2 prepared in this invention or rhBMP-2-loaded microspheres can combined or be mixed with carriers by physical adsorption, investment under homogeneous or non-homogeneous phase to prepare bioactive hard tissue repair biomaterials. The results showed that, the fabricated materials could control the release of protein with desirable release rate.

The carriers include inorganic biomaterials (such as hydroxyapatite HAP, Tricalcium Phosphate, Calcium Phosphate Cement or CPC, Calcium Polyphosphate, Coral, Bioglass, Glass-ceramic or their compounds), polymers (including Polylactic Acid, Polyglycolic Acid, Polyβ-hydroxy butyrate, polyorthoester, polycarbonate or their compounds), natural biomaterials (natural proteins such as collagen, gelatin and polysaccharide including chitosan, chondroitin sulfate, hyaluronic acid, glycosaminoglycan) or mutual compounds. The amount of the carrier is 0-3000 times of that of rhBMP-2, on basis of the weight of rhBMP-2.

The main advantages of this invention include:
(a) The genetic technology based on prokaryotic expression system is convenient and suitable for large-scale production in industry.
(b) Compared with the rhBMP-2 genes without optimization or optimized by software alone, the product yield of optimized rhBMP-2 genes of this invention is increased by 50% in the recombinant *E. coli* strain.
(c) In addition to the optimized natural hBMP-2, the gene of long chain rhBMP-2 is also constructed and optimized, which has the advantages of high renaturation efficiency and high yield after purification as compared with rhBMP-2 mature peptide.
(d) The rhBMP-2 prepared by this invention not only has better osteoinductivity, but also has good stability, high expression efficiency, low cost, so that it is an ideal bone growth factor and can be applied to vertebral surgery, cosmetic surgery, stomatology, orthopedics (especially at the aspect of bone nonunion and delayed union) alone or in combination with carriers.

The invention is further illustrated by the following examples. It is appreciated that these examples are only intended to illustrate the invention, but not to limit the scope of the invention. The experimental methods in the following examples are performed under routine conditions, e.g., just like those described by Sambrook. et al., in Molecule Cloning: A Laboratory Manual, New York: Cold Spring Harbor Laboratory Press, 1989, or as instructed by the manufacturers, unless otherwise specified.

Example 1

The Optimization of hBMP-2 Gene of Mature Peptides by Codon Optimization Software, Construction of Engineered Bacteria and Preparation of rhBMP-2

1. Optimization of DNA Sequence of hBMP-2

According to the *E. coli* codon usage frequency, the DNA sequence of hBMP-2 was optimized by software to obtain the optimized rhBMP-2 gene (SEQ ID NO: 3).

2. Construction of Expression Vectors

Restriction enzyme cleavage site and translation initiation nucleotide codon (GAATTCATG) were added to the 5' terminal of DNA sequence of optimal rhBMP-2 obtained in step 1. The double stop codon and restriction enzyme cleavage site (TAGTAGGGATCC) were added to the 3' terminal. The gene was synthesized and inserted into the conventional vector pBV220 (commercially available from Jinwei Biotech Co., Shanghai) at EcoRI/BamHI sites. The rhBMP-2 expression vector was obtained, named pRB-hBMP-2-2. The inserted elements were confirmed by restriction enzyme digestion and sequencing.

3. Construction, Verification and Storage of Engineered Bacteria

Competent *E. coli* cell (JM109) was prepared by the conventional calcium chloride method. The competent *E. coli* was transformed by the expression vector obtained in step 2. From the LB plate with appropriate antibiotics, several positive colonies were picked and cultured overnight in LB. Plasmid DNA was isolated and analyzed by restriction enzyme digestion and sequencing to confirm the presence of the correct expression vector. Once the correct clone was identified, the colony was purified and inoculated into flasks containing LB culture medium with glucose and antibiotics, cultured for 15 hrs under the condition of 180 rpm and 30° C. in air bath shaker. Sterile glycerol was mixed with the culture to make a glycerol stock of the recombinant cell with the final glycerol concentration of 15%. The glycerol stock was transferred to a cryovial and stored at −80° C. freezer.

4. Culture of Engineered Bacteria

From the glycerol stock of the engineered bacteria, the original colony was streaked out for single colonies on an LB plate containing appropriate antibiotics, A single colony was isolated and inoculated into LB culture medium containing 10 g/l tryptone, 5 g/l yeast extract, 5 g/l NaCl and 100 µg/mL penbrtin. After 8 hrs' culture under the condition of 180 rpm and 30° C. in air bath shaker, the culture was inoculated into LB culture medium with volume ratio of 1:10 and continued culture for 4 hrs under the condition of 180 rpm, 30° C., and pH 7.0±0.2. After that, temperature was raised to 42° C. to culture for 6 hrs. At the end of culture, the medium was centrifuged (7500 rpm) at 4±2° C., and bacteria were collected and disrupted. The polyacrylamide gel electrophoresis (PAGE) was run to analyze the cell lysis. Compared to recombinant bacteria before induction and blank bacteria without plasmid, a clear band corresponding to molecular weight of 13 KD was observed, which indicated that the objective protein was obtained.

5. Extracting and Washing of Inclusion Bodies

The bacteria collected in step 4 was mixed with TE solution at the ratio of 1 g:10 ml, and then lysozyme was added at the ratio of 1 g:1 mg. The bacteria were broken by cell disruption technique and centrifuged at 10000 rpm. After that, the precipitate was collected and mixed with washing buffer at the ratio of 1 g:20 ml (precipitate: washing buffer). After 2 hrs stirring, the cell lysis was collected by centrifugation at 4±2° C., washed again with washing buffer. Then, the cell lysis was washed with 10 mM Tris (pH 7.5) solution and precipitated by centrifugation to obtain inclusion bodies.

6. Solubilization and Renaturation of Inclusion Bodies

Lysis solution comprising 6 M Gu-HCl, 20 mM PBS, 10 mM DTT was added at the ratio of 1 g:10 ml (inclusion bodies: lysis solution), stirred to dissolve inclusion body precipitate for 8 hrs at 4±2° C., centrifuged for 30 min at 10000 rpm and 4±2° C. The supernatant was collected, diluted to protein level of 0.1 mg/ml, then mixed with refolding solution to renature for 15 d. The refolding solution contained 20 mM $Na_2HPO_4.12H_2O$, 1.5 mM $NaH_2PO_4.2H_2O$, 140 mM NaCl, 5 mM EDTA and 1 mM glutathione.

7. Purification of Protein

Bioactive dimer of rhBMP-2 was recovered from refolding solution by conventional purification processes, such as anion-exchange chromatography, cation-exchange chromatography, and molecular-exclusion chromatography. And then the obtained rhBMP-2 was lyophilized at −30~7° C.

The results determined by non-reducing SDS-PAGE indicated that the protein purity was above 95% and the molecular weight was about 26 KD. HLPC analysis also showed that the purity was above 95%. Also, the sequences of N-terminus and C-terminus were the same as those deduced from the nucleotide sequences. The average yield of rhBMP-2 was 5.3 mg/L.

8. Test of Bioactivity

The bioactivity of the BMP-2 was detected by in vitro cell culture and in vivo ectopic bone formation.

(1) In Vitro Cell Culture

C2C12 myoblasts were maintained in Dulbecco's modified Eagle's medium (DMEM) containing 10% fetal bovine serum at 37° C. in a humidified atmosphere of 5% $CO_2$ in air. For all treatments, cells were cultured in 96-well plates at a density of $1.0 \times 10^4$ cells/mL in 100 µL of DMEM medium for 3 days. Then, the culture medium was removed and replaced with 200 µL of DMEM with rhBMP-2 dimer or monomer (control) at the concentrations ranging from 1 μg/mL to 12 μg/mL. Cells without any rhBMP-2 treatment were used as blank control. Experiments were performed in triplicate. After 3 days, medium was removed. The C2C12 cells were washed and incubated with 50 μL of 1% Nonidet P-40 solution (NP-40, constructed by ALP buffer solution) at room temperature (RT) for 1 h to obtain cell lysate. After that, 50 μL of 1 mg/mL p-nitrophenylphosphate (Sangon, Shanghai, China) substrate solution (pH 9) was added. The reaction was terminated 15 min later by adding 100 μL of 0.2 N NaOH, and the absorbance value was measured at the wavelength of 405 nm using a microplate reader (SPECTRAmax 384, Molecular Devices, USA). The results indicated that in comparison with the control or blank control, within the concentration range tested, ALP activity was greatly induced by rhBMP-2 dimer in a dose-dependent manner, demonstrating that rhBMP-2 dimer has good osteoinductive activity. In contrast, rhBMP-2 monomer did not induce detectable ALP activity.

(2) In Vivo Evaluation 0.25 mg of the rhBMP-2 obtained was implanted to leg muscle of Kunming mouse. The results demonstrated that the ectopic bone formed. In contrast, no new bon could be found in the control group (without rhBMP-2).

Example 2

Further Optimization of hBMP-2 Mature Peptide, Construction of Engineered Bacteria and Preparation of rhBMP-2

1. Optimization of DNA Sequence of hBMP-2

According to the *E. coli* codon usage frequency, the optimized DNA sequence of hBMP-2 (SEQ ID NO: 3) was optimized by software. Based on the DNA sequence (SEQ ID NO: 3), another optimized DNA sequence of rhBMP-2 (SEQ ID NO: 4) was obtained by further replacement of parts of nucleotide according to the calculated value.

2. Construction of Expression Vectors

Restriction enzyme cleavage site and translation initiation nucleotide codon (GAATTCATG) were added to the 5' terminal of DNA sequence of optimal rhBMP-2 obtained in step 1. The double stop codon and restriction enzyme cleavage site (TAGTAGGGATCC) were added to the 3' terminal. The gene was synthesized and inserted into the conventional vector pBV220 (commercially available from Jinwei Biotech Co., Shanghai) at EcoRI/BamHI sites. The rhBMP-2 expressing vector was obtained, named pRB-hBMP-2-1 (FIG. 1). The inserted elements were confirmed by restriction enzyme design and sequencing.

3. Construction, Verification and Storage of Engineered Bacteria

Competent *E. coli* cell (JM109) was prepared by the conventional method of calcium chloride. The competent *E. coli* was transformed by the expression vector obtained in step 2. From the LB plate with appropriate antibiotics, several positive colonies were picked and cultured overnight in LB. Plasmid DNA was isolated and analyzed by restriction enzyme digestion and sequencing to confirm the presence of the correct expression vector. Once the correct clone was identified, the colony was purified and inoculated into flasks containing LB culture medium with glucose and antibiotics, cultured for 15 hrs under the condition of 180 rpm and 30° C. in air bath shaker. Sterile glycerol was mixed with the culture to make a glycerol stock of the recombinant cell with the final glycerol concentration of 15%. The glycerol stock was transferred to a cryovial and stored at −80° C. freezer.

4. Culture of Engineered Bacteria

From the glycerol stock of the engineered bacteria, the original colony was streaked out for single colonies on an LB plate containing appropriate antibiotics, a single colony was isolated and inoculated into LB culture medium containing 10 g/l tryptone, 5 g/l yeast extract, 5 g/l NaCl and 100 μg/mL penbrtin. After 8 hrs culture under the condition of 180 rpm and 30° C. in air bath shaker, the culture was inoculated into LB culture medium with volume ratio of 1:10 for another 4 hrs under the condition of 180 rpm, 30° C. and pH 7.0±0.2. After that, temperature was raised to 42° C. to continue culture for 6 hrs. At the end of culture, medium was centrifuged at 7500 rpm, 4±2° C., and bacteria were collected and disrupted. The polyacrylamide gel electrophoresis (PAGE) was run to analyze the cell lysis. The result indicated that compared to the recombinant bacteria before induction and blank bacteria without plasmid, a clear band corresponding to the molecular weight of 13 KD was observed.

5. Extracting and Washing of Inclusion Bodies

The bacteria collected in step 4 was mixed with TE solution at the ratio of 1 g:10 ml, then lysozyme was added at the ratio of 1 g:1 mg. The bacteria were broken by cell disruption technique and centrifuged at 10000 rpm. The precipitate was collected and mixed with washing buffer at the ratio of 1 g:20 ml (precipitate: washing buffer). After 2 hrs stirring, the cell lysis was collected by centrifugation at 4±2° C., washed again with washing buffer. Then, the cell lysis was washed with 10 mM Tris (pH 7.5) solution and precipitated by centrifugation to obtain inclusion bodies.

6. Solubilization and Renaturation of Inclusion Bodies

Lysis solution comprising 6 M Gu-HCl, 20 mM PBS, 10 mM DTT was added at the ratio of 1 g:10 ml (inclusion bodies: lysis solution), stirred to dissolve inclusion body precipitate for 8 hrs at 4±2° C., centrifuged for 30 min at 10000 rpm and 4±2° C. The supernatant was collected, diluted to protein level of 0.1 mg/ml, then mixed with refolding solution to renature for 15 d. The refolding solution contained 20 mM $Na_2HPO_4 \cdot 12H_2O$, 1.5 mM $NaH_2PO_4 \cdot 2H_2O$, 140 mM NaCl, 5 mM EDTA and 1 mM glutathione.

7. Purification of Protein

Bioactive dimer of rhBMP-2 was recovered from refolding solution by conventional purification processes, such as anion-exchange chromatography, cation-exchange chromatography, and molecular-exclusion chromatography. And then the obtained rhBMP-2 was lyophilized at −30~7° C.

The results of non-reducing SDS-PAGE (FIG. 2) indicated that the protein purity was above 95% and the molecular weight was about 26 KD. HLPC analysis also showed that the purity was above 95%. Also, the amino acid sequences of N-terminus and C-terminus were the same as those deduced from the nucleotide sequences.

The average yield of rhBMP-2 was 7.62 mg/L, indicating that the expression level of gene sequence of SEQ ID NO: 4 was higher than that of SEQ ID NO: 3.

8. Test of Bioactivity

The bioactivity of the BMP-2 was detected by in vitro cell culture and in vivo ectopic bone formation.

(1) In Vitro Cell Culture

C2C12 cells are plated into 96 well tissue culture plates at a density of $1.0 \times 10^4$ cells/mL in 100 μL of media (DMEM with 10% heat inactivated fetal calf serum, 100 u antibiotics. The cells are cultured at 37° C. in humidified atmosphere of 5% $CO_2$/95% air. After 3 days incubation, the culture media was removed and replaced with 200 μL DMEM medium containing rhBMP-2 dimer at the range from 1 μg/mL to 12 μg/mL. The equal volume DMEM media with rhBMP-2 monomer at the same concentration and without rhBMP-2 were used as control. Each concentration was conducted in triplicate. After 3 days, plates are removed from the 37° C. incubator and the test media are removed from the cells. The C2C12 cells were washed 2 times with PBS. Then, 50 μL 1% Nonidet P-40 solution (NP-40, constructed by ALP buffer solution) was added to each well at room temperature (RT) for 1 h to obtain cell lysate. After that, 50 μL of 1 mg/mL p-nitrophenylphosphate (Sangon, Shanghai, China) substrate solution (pH 9) was added and incubated for another 15 min at RT. The reaction was quenched by adding 100 μL of 0.2 N NaOH, and the absorbance of ALP was quantified at the wavelength of 405 nm using a microplate reader (SPECTRAmax 384, Molecular Devices, USA). The results (FIG. 3) indicated that within the concentration from 1 μg/mL to 12 μg/mL, the BMP-2 tested showed higher ALP activity than that of the rhBMP-2 obtained in Example 1. But the rhBMP-2 monomer or without rhBMP-2 groups had no detectable ALP activity.

(2) In Vivo Evaluation 0.25 mg of the rhBMP-2 obtained was implanted to leg muscle of Kunming mouse. The results (FIG. 4) demonstrated that, compared with the rhBMP-2 obtained in Example 1, the amount of ectopic bone formation increased, indicating that the rhBMP-2 obtained had higher osteoinductivity than that obtained in Example 1. In contrast, no new bon could be found in the control group (without rhBMP-2).

Figure 5:
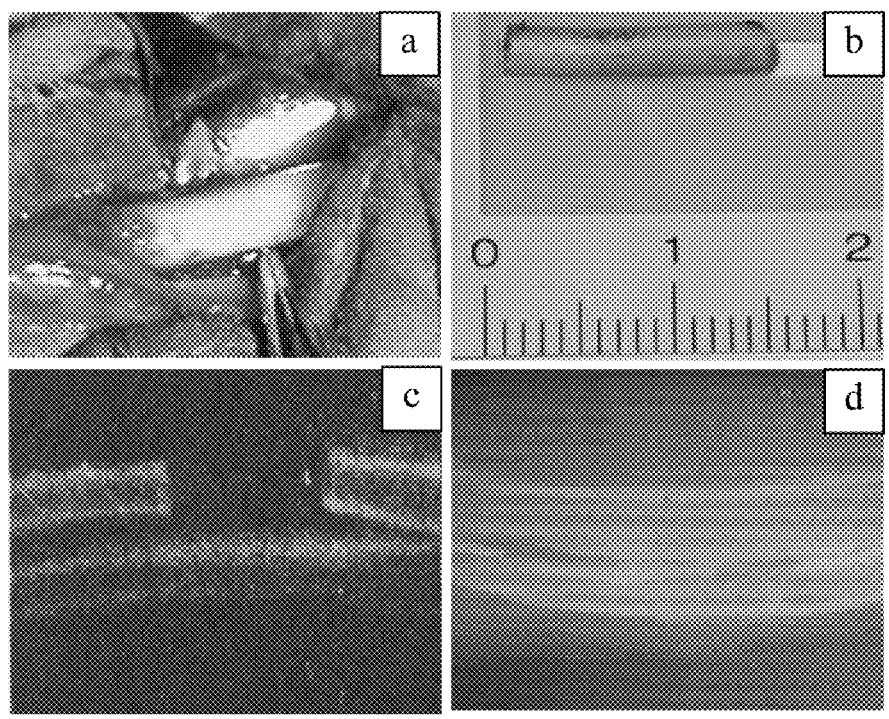
FIG. 5 shows the in situ bone formation. (a) bone extracting process, (b) the extracted bone with the length of 1.5 cm, (c) the bone radius segment defection before implantation, (d) 3 month postoperation

The rhBMP-2 prepared was implanted to radius segment defection with the length of 1.5 cm in New Zealand rabbits. The results (FIG. 5) demonstrated that the rhBMP-2 showed excellent in-situ osteoinductive activity. After 12 weeks implantation, 1.5 cm radius defection could be filled with new bone matrix completely, and almost recovered to normal morphology, and formed normal cortical bone. In contrast, no new bon could be found in the control group (without rhBMP-2).

Example 3

For Comparison cDNA Synthesis of Human BMP-2 Mature Peptide, Construction of Engineered Bacteria and Preparation of rhBMP-2 (Without Optimization Steps)

1. The Genetic Sequence of Human BMP-2

The nucleotide sequence of human BMP-2 was showed in SEQ ID NO: 1.

2. Construction of Expression Vectors

Restriction enzyme cleavage site and translation initiation nucleotide codon (GAATTCATG) were added to the 5' terminal of DNA sequence of hBMP-2 mentioned in step 1. The double stop codon and restriction enzyme cleavage site (TAGTAGGGATCC) were added to the 3' terminal. The gene was synthesized and inserted into vector pBV220 by restriction digestion and ligation. The hBMP-2 expressing plasmid was obtained, named pRB-hBMP-3. The inserted elements were confirmed by digestion and sequencing.

3. Construction, Verification and Storage of Engineered Bacteria

Competent *E. coli* cell (JM109) was prepared by the conventional method of calcium chloride. The competent *E. coli* was transformed by the expression vector obtained in step 2. From the LB plate with appropriate antibiotics, several positive colonies were picked and cultured overnight in LB. Plasmid DNA was isolated and analyzed by restriction enzyme digestion and sequencing to confirm the presence of the correct expression vector. Once the correct clone was identified, the colony was purified and inoculated into flasks containing LB culture medium with glucose and antibiotics, cultured for 15 hrs at 180 rpm and 30° C. in air bath shaker. Sterile glycerol was mixed with the culture to make a glycerol stock of the recombinant cell with the final glycerol concentration of 15%. The glycerol stock was transferred to a cryovial and stored at −80° C. freezer.

4. Culture of Engineered Bacteria

From the glycerol stock of the engineered bacteria, the original colony was streaked out for single colonies on an LB plate containing appropriate antibiotics, A single colony was isolated and inoculated into LB culture medium containing 10 g/l tryptone, 5 g/l yeast extract, 5 g/l NaCl and 100 μg/mL penbrtin. After 8 hrs culture under the condition of 180 rpm and 30° C. in air bath shaker, the culture was inoculated into LB culture medium with volume ratio of 1:10 for another 4 hrs under the condition of 180 rpm, 30° C. and pH 7.0±0.2. After that, temperature was raised to 42° C. to continue culture for 6 hrs. At the end of culture, medium was centrifuged at 7500 rpm, 4±2° C., and bacteria were collected and disrupted. The polyacrylamide gel electrophoresis (PAGE) was run to analyze the cell lysis. The result indicated that compared to the recombinant bacteria before induction and blank bacteria without plasmid, a clear band corresponding to molecular weight of the target protein (13 KD) was observed.

5. Extracting and Washing of Inclusion Bodies

The bacteria collected in step 4 was mixed with TE solution at the ratio of 1 g:10 ml, then lysozyme was added at the ratio of 1 g:1 mg. The bacteria were broken by cell disruption technique, centrifuged at 10000 rpm. The precipitate was collected and mixed with washing buffer at the ratio of 1 g:20 ml (precipitate: washing buffer). After 2 hrs stirring, the cell lysis was centrifuged and collected at 412° C., washed again with washing buffer. Then, 10 mM Tris (pH 7.5) solution was added at a ratio of 1 g precipitate:20 mL Tris, washed and centrifuged to collect inclusion bodies.

6. Solubilization and Renaturation of Inclusion Bodies

Lysis solution comprising 6 M Gu-HCl, 20 mM PBS, 10 mM DTT was added at the ratio of 1 g:10 ml (inclusion bodies: lysis solution), stirred to dissolve inclusion body precipitate for 8 hrs at 4±2° C., centrifuged for 30 min at 10000 rpm and 4±2° C. The supernatant was collected, diluted to protein level of 0.1 mg/ml, and then mixed with refolding solution to renature for 10 d. The refolding solution contained 20 mM $Na_2HPO_4.12H_2O$, 1.5 mM $NaH_2PO_4.2H_2O$, 140 mM NaCl, 5 mM EDTA and 1 mM glutathione.

7. Purification of Protein

Bioactive dimer of rhBMP-2 was recovered from refolding solution by conventional purification processes, such as anion-exchange chromatography, cation-exchange chromatography, and molecular-exclusion chromatography. And then the obtained rhBMP-2 was lyophilized at −30~7° C.

The results determined by non-reducing SDS-PAGE indicated that the protein purity was above 95% and the molecular weight was about 26 KD. HLPC analysis also showed that the purity was above 95%. Also, the amino acid sequences of N-terminus and C-terminus were the same as those deduced from the nucleotide sequences.

The average yield of rhBMP-2 was 4.95 mg/L.

8. Test of Bioactivity

The bioactivity of the BMP-2 was detected by in vitro cell culture and in vivo ectopic bone formation.

(1) In Vitro Cell Culture

C2C12 cells are plated into 96 well tissue culture plates at a density of $1.0\times10^4$ cells/mL in 100 μL of media (DMEM with 10% heat inactivated fetal calf serum, 100 u antibiotics. The cells are cultured at 37° C. in humidified atmosphere of 5% $CO_2$/95% air. After 3 days incubation, the culture media was removed and replaced with 200 μL DMEM medium containing rhBMP-2 dimer at the range from 1 μg/mL to 12 μg/mL. The equal volume DMEM media with rhBMP-2 monomer at the same concentration and without rhBMP-2 were used as control. Each concentration was conducted in triplicate. After 3 days, plates are removed from the 37° C. incubator and the test media are removed from the cells. The C2C12 cells were washed 2 times with PBS. Then, 50 μL 1% Nonidet P-40 solution (NP-40, constructed by ALP buffer solution) was added to each well at room temperature (RT) for 1 h to obtain cell lysate. After that, 50 μL of 1 mg/mL p-nitrophenylphosphate (Sangon, Shanghai, China) substrate solution (pH 9) was added and incubated for another 15 min at RT. The reaction was quenched by adding 100 μL of 0.2 N NaOH, and the absorbance of ALP was quantified at the wavelength of 405 nm using a microplate reader (SPECTRAmax 384, Molecular Devices, USA). The results indicated that within the concentration from 1 μg/mL to 12 μg/mL, the rhBMP-2 produced showed lower ALP activity than that of the rhBMP-2 obtained in Example 1 and example 2. But the rhBMP-2 monomer or without rhBMP-2 groups had no detectable ALP activity.

(2) In Vivo Evaluation 0.25 mg of the rhBMP-2 obtained was implanted to leg muscle of Kunming mouse. The results demonstrated that, the amount of ectopic bone formation decreased compared to that formed in Example 1 and Example 2, indicating that the osteoinductivity of the rhBMP-2 obtained was lower than that obtained in Example 1 and Example 2. In contrast, no new bon could be found in the control group (rhBMP-2 monomer).

Example 4

Optimization of Long Chain Human BMP-2 Genes by Single Codon Software, Construction of Genetic Engineered Bacteria and Preparation of rhBMP-2

1. Optimization of Long Chain Human BMP-2 Genes

Based on the DNA sequence of rhBMP-2 mature peptide optimized by software (SEQ ID NO: 3), nucleotides (SEQ ID NO: 5, 1-48, AAA CGT CAT GAT GGC AAA GGC CAT CCG CTG CAT AAA CGC GAA AAA CGC) corresponding to 16 amino acide residues of natural hBMP-2 prepeptide (SEQ ID NO: 6, 1-16, Lys Arg His Asp Gly Lys Gly His Pro Leu His Lys Arg Glu Lys Arg) were added to the 5' terminal to obtain the DNA sequence of long chain rhBMP-2 gene (SEQ ID NO: 7).

2. Construction of Expression Vectors

Restriction enzyme cleavage site and translation initiation nucleotide codon (GAATTCATG) were added to the 5' terminal of DNA sequence of optimal long chain rhBMP-2 obtained in step 1 (SEQ ID NO: 7). The double stop codon and restriction enzyme cleavage site (TAGTAGGGATCC) were added to the 3' terminal. The gene was synthesized and inserted into vector pBV220 by restriction digestion and ligation. The rhBMP-2 expressing plasmid was obtained and named pRB-hBMP-L-2. The inserted elements were confirmed by digestion and sequencing.

3. Construction, Verification and Storage of Engineered Bacteria

Competent *E. coli* cell (JM109) was prepared by the conventional method of calcium chloride. The competent *E. coli* was transformed by the expression vector obtained in step 2. From the LB plate with appropriate antibiotics, several positive colonies were picked and cultured overnight in LB. Plasmid DNA was isolated and analyzed by restriction enzyme digestion and sequencing to confirm the presence of the correct expression vector. Once the correct clone was identified, the colony was purified and inoculated into flasks containing LB culture medium with glucose and antibiotics, cultured for 15 hrs under the condition of 180 rpm and 30° C. in air bath shaker. Sterile glycerol was mixed with the culture to make a glycerol stock of the recombinant cell with the final glycerol concentration of 15%. The glycerol stock was transferred to a cryovial and stored at −80° C. freezer.

4. Culture of Engineered Bacteria

From the glycerol stock of the engineered bacteria, the original colony was streaked out for single colonies on an LB plate containing appropriate antibiotics, A single colony was isolated and inoculated into flasks containing LB culture medium containing 10 g/l tryptone, 5 g/l yeast extract, 5 g/l NaCl and 100 μg/mL penbrtin. After 8 hrs culture under the condition of 180 rpm and 30° C. in air bath shaker, the culture was inoculated into LB culture medium with volume ratio of 1:10 for another 4 hrs under the condition of 180 rpm, 30° C. and pH 7.0±0.2. After that, temperature was raised to 42° C. to continue culture for 6 hrs. At the end of culture, medium was centrifuged at 7500 rpm, 4±2° C., and bacteria were collected and disrupted. The polyacrylamide gel electrophoresis (PAGE) was run to analyze the cell lysis. The result indicated that compared to the recombinant bacteria before induction and blank bacteria without plasmid, a clear band corresponding to molecular weight of the target protein (13 KD) was observed.

5. Extracting and Washing of Inclusion Bodies

The bacteria collected in step 4 was mixed with TE solution at the ratio of 1 g:10 ml, then lysozyme was added at the ratio of 1 g:1 mg. The bacteria were broken by cell disruption technique, centrifuged at 10000 rpm. The precipitate was collected and mixed with washing buffer at the ratio of 1 g:20 ml (precipitate: washing buffer). After 2 hrs stirring, the cell lysis was centrifuged and collected at 4±2° C., washed again with washing buffer. Then, 10 mM Tris (pH 7.5) solution was added at a ratio of 1 g precipitate:20 mL Tris, washed, and centrifuged to collect inclusion bodies.

6. Solubilization and Renaturation of Inclusion Bodies

Lysis solution comprising 6 M Gu-HCl, 20 mM PBS, 10 mM DTT was added at the ratio of 1 g:10 ml (inclusion bodies: lysis solution), stirred to dissolve inclusion body precipitate for 8 hrs at 4±2° C., centrifuged for 30 min at 10000 rpm and 4±2° C. The supernatant was collected, diluted to protein level of 0.1 mg/ml, then mixed with refolding solution to renature for 10 d. The refolding solution contained 20 mM $Na_2HPO_4.12H_2O$, 1.5 mM $NaH_2PO_4.2H_2O$, 140 mM NaCl, 5 mM EDTA and 1 mM glutathione.

7. Purification of Protein

Bioactive dimer of rhBMP-2 was recovered from refolding solution by conventional purification processes, such as anion-exchange chromatography, cation-exchange chromatography, and molecular-exclusion chromatography. And then the obtained rhBMP-2 was lyophilized at −30~7° C.

The results determined by non-reducing SDS-PAGE indicated that the protein purity was above 95% and the molecular weight was about 26 KD. HLPC analysis also showed that the purity was above 95%. Also, the amino acid sequences of N-terminus and C-terminus were the same as those deduced from the nucleotide sequences.

The average yield of rhBMP-2 was 7.02 mg/L.

7. Test of Bioactivity

The bioactivity of the BMP-2 was detected by in vitro cell culture and in vivo ectopic bone formation.

(1) In Vitro Cell Culture

C2C12 cells are plated into 96 well tissue culture plates at a density of $1.0 \times 10^4$ cells/mL in 100 μL of media (DMEM with 10% heat inactivated fetal calf serum, 100 u antibiotics. The cells are cultured at 37° C. in humidified atmosphere of 5% $CO_2$/95% air. After 3 days incubation, the culture media was removed and replaced with 200 μL DMEM medium containing rhBMP-2 dimer at the range from 1 μg/mL to 12 μg/mL. The equal volume DMEM media with rhBMP-2 monomer at the same concentration and without rhBMP-2 were used as control. Each concentration was conducted in triplicate. After 3 days, plates are removed from the 37° C. incubator and the test media are removed from the cells. The C2C12 cells were washed 2 times with PBS. Then, 50 μL 1% Nonidet P-40 solution (NP-40, constructed by ALP buffer solution) was added to each well at room temperature (RT) for 1 h to obtain cell lysate. After that, 50 μL of 1 mg/mL p-nitrophenylphosphate (Sangon, Shanghai, China) substrate solution (pH 9) was added and incubated for another 15 min at RT. The reaction was quenched by adding 100 μL of 0.2 N NaOH, and the absorbance of ALP was quantified at the wavelength of 405 nm using a microplate reader (SPECTRA-max 384, Molecular Devices, USA). The results indicated that within the concentration from 1 μg/mL to 12 μg/mL, the rhBMP-2 produced showed higher ALP activity than that of the rhBMP-2 obtained in Example 1. But the rhBMP-2 monomer or without rhBMP-2 groups had no detectable ALP activity.

(2) In Vivo Evaluation 0.25 mg of the rhBMP-2 obtained was implanted to leg muscle of Kunming mouse. The results demonstrated that, the amount of ectopic bone formation increased compared to that formed in Example 1, indicating that the osteoinductivity of the rhBMP-2 obtained was better than that obtained in Example 1. In contrast, no new bon could be found in the control group (without rhBMP-2).

Example 5

Optimization of Long Chain hBMP-2 Genes, Construction of Genetic Engineered Bacteria and Preparation of rhBMP-2

1. Optimization of Long Chain hBMP-2 Genes

Based on the DNA sequence of rhBMP-2 mature peptide optimized by software (SEQ ID NO: 4), nucleotides (SEQ ID NO: 5, 1-48, AAA CGT CAT GAT GGC AAA GGC CAT CCG CTG CAT AAA CGC GAA AAA CGC) corresponding to 16 amino acide residues of natural hBMP-2 prepeptide (SEQ ID NO: 6, 1-16, Lys Arg His Asp Gly Lys Gly His Pro Leu His Lys Arg Glu Lys Arg) were added to the 5' terminal to obtain the DNA sequence of long chain rhBMP-2 gene (SEQ ID NO: 8).

2. Construction of Expression Vectors

Figure 6:
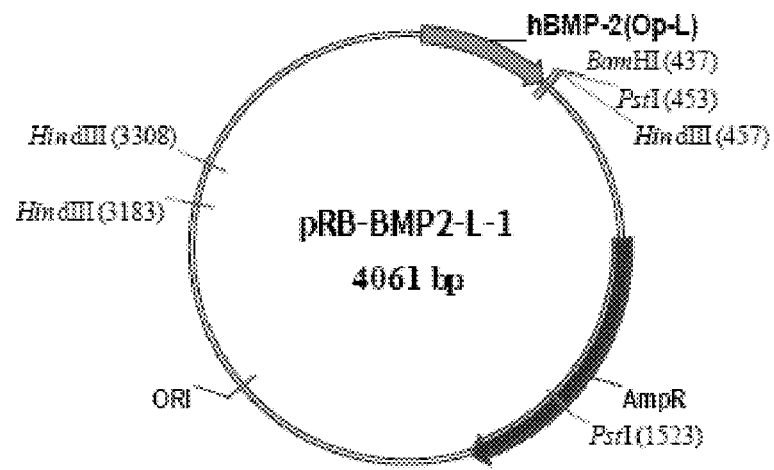
FIG. 6 shows the optimal genetic expression plasmid pRB-BMP-2-L-1 (4061 bp) of long chain rhBMP-2.

Restriction enzyme cleavage site and translation initiation nucleotide codon (GAATTCATG) were added to the 5' terminal of DNA sequence of optimal long chain hBMP-2 obtained in step 1 (SEQ ID NO: 8). The double stop codon and restriction enzyme cleavage site (TAGTAGGGATCC) were added to the 3' terminal. The gene was synthesized and inserted into vector pBV220 by digestion and ligation. The rhBMP-2 expressing plasmid was obtained, named pRB-hBMP-L-1(FIG. 6). The inserted elements were confirmed by digestion and sequencing.

3. Construction, Verification and Storage of Engineered Bacteria

Competent *E. coli* cell (JM109) was prepared by the conventional method of calcium chloride. The competent *E. coli* was transformed by the expression vector obtained in step 2. From the LB plate with appropriate antibiotics, several positive colonies were picked and cultured overnight in LB. Plasmid DNA was isolated and analyzed by restriction enzyme digestion and sequencing to confirm the presence of the correct expression vector. Once the correct clone was identified, the colony was purified and inoculated into flasks containing LB culture medium with glucose and antibiotics, cultured for 15 hrs at 180 rpm and 30° C. in air bath shaker. Sterile glycerol was mixed with the culture to make a glycerol stock of the recombinant cell with the final glycerol concentration of 15%. The glycerol stock was transferred to a cryovial and stored at −80° C. freezer.

4. Culture of Engineered Bacteria

From the glycerol stock of the engineered bacteria, the original colony was streaked out for single colonies on an LB plate containing appropriate antibiotics, A single colony was isolated and inoculated into flasks containing LB culture medium containing 10 g/l tryptone, 5 g/l yeast extract, 5 g/l NaCl and 100 μg/mL penbrtin. After 8 hrs culture under the conditions of 180 rpm and 30° C. in air bath shaker, the culture was inoculated into LB culture medium with volume ratio of 1:10 for another 4 hrs under the condition of 180 rpm, 30° C. and pH 7.0±0.2. After that, temperature was raised to 42° C. to continue culture for 6 hrs. At the end of culture, medium was centrifuged at 7500 rpm, 4±2° C., and bacteria were collected and disrupted. The polyacrylamide gel electrophoresis (PAGE) was run to analyze the cell lysis. The result indicated that compared to the recombinant bacteria before induction and blank bacteria without plasmid, a clear band corresponding to molecular weight of the target protein (13 KD) was observed.

5. Extracting and Washing of Inclusion Bodies

The bacteria collected in step 4 was mixed with TE solution at the ratio of 1 g:10 ml, then lysozyme was added at the ratio of 1 g:1 mg. Bacteria were broken by cell disruption technique, centrifuged at 10000 rpm. The precipitate was collected and mixed with washing buffer at the ratio of 1 g:20 ml (precipitate: washing buffer). After 2 hrs stirring, the cell lysis was centrifuged and collected at 4±2° C., washed again with washing buffer. Then, 10 mM Tris (pH 7.5) solution was added at a ratio of 1 g precipitate:20 mL Tris, washed and centrifuged to collect inclusion bodies.

6. Solubilization and Renaturation of Inclusion Bodies

Lysis solution comprising 6 M Gu-HCl, 20 mM PBS, 10 mM DTT was added at the ratio of 1 g:10 ml (inclusion bodies: lysis solution), stirred to dissolve inclusion body precipitate for 8 hrs at 4±2° C., centrifuged for 30 mM at 10000 rpm and 4±2° C., The supernatant was collected, diluted to protein level of 0.1 mg/ml, then mixed with refolding solution to renature for 10 d. The refolding solution contained 20 mM $Na_2HPO_4.12H_2O$, 1.5 mM $NaH_2PO_4.2H_2O$, 140 mM NaCl, 5 mM EDTA and 1 mM glutathione.

7. Purification of Protein

Bioactive dimer of rhBMP-2 was recovered from refolding solution by conventional purification processes, such as anion-exchange chromatography, cation-exchange chromatography, and molecular-exclusion chromatography. And then the obtained rhBMP-2 was lyophilized at −30~7° C.

Figure 7:
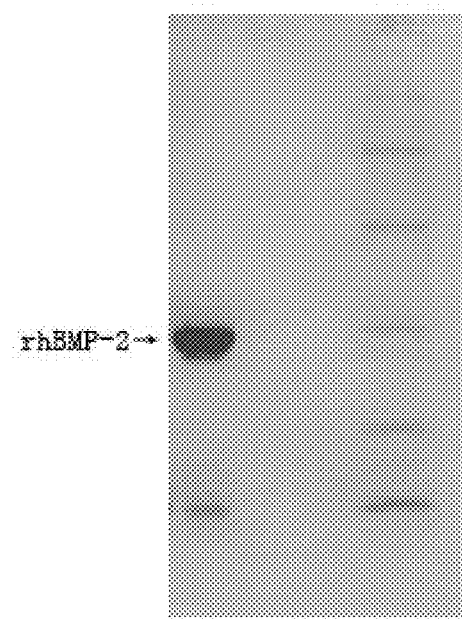
FIG. 7 shows the electrophoresis of long chain rhBMP-2.

The results determined by non-reducing SDS-PAGE (FIG. 7) indicated that the protein purity was above 95% and the molecular weight was about 26 KD. HLPC analysis also showed that the purity was above 95%. Also, the amino acid sequences of N-terminus and C-terminus were the same as those deduced from the nucleotide sequences.

The average yield of rhBMP-2 was 10.05 mg/L, indicating that the sequence of SEQ ID NO: 8 is superior to that of SEQ ID NO: 7.

8. Test of Bioactivity

The bioactivity of the BMP-2 was detected by in vitro cell culture and in vivo ectopic bone formation.

(1) In Vitro Cell Culture

C2C12 cells are plated into 96 well tissue culture plates at a density of $1.0 \times 10^4$ cells/mL in 100 µL of media (DMEM with 10% heat inactivated fetal calf serum, 100 u antibiotics. The cells are cultured at 37° C. in humidified atmosphere of 5% $CO_2$/95% air. After 3 days incubation, the culture media was removed and replaced with 200 µL DMEM medium containing rhBMP-2 dimer at the range from 1 µg/mL to 12 µg/mL. The equal volume DMEM media with rhBMP-2 monomer at the same concentration and without rhBMP-2 were used as control. Each concentration was conducted in triplicate. After 3 days, plates are removed from the 37° C. incubator and the test media are removed from the cells. The C2C12 cells were washed 2 times with PBS. Then, 50 µL 1% Nonidet P-40 solution (NP-40, constructed by ALP buffer solution) was added to each well at room temperature (RT) for 1 h to obtain cell lysate. After that, 50 µL of 1 mg/mL p-nitrophenylphosphate (Sangon, Shanghai, China) substrate solution (pH 9) was added and incubated for another 15 min at RT. The reaction was quenched by adding 100 µL of 0.2 N NaOH, and the absorbance of ALP was quantified at the wavelength of 405 nm using a microplate reader (SPECTRAmax 384, Molecular Devices, USA). The results indicated that within the concentration from 1 µg/mL to 12 µg/mL, the rhBMP-2 produced showed higher ALP activity than that of the rhBMP-2 obtained in Example 4. But the rhBMP-2 monomer or without rhBMP-2 groups had no detectable ALP activity.

Figure 8:
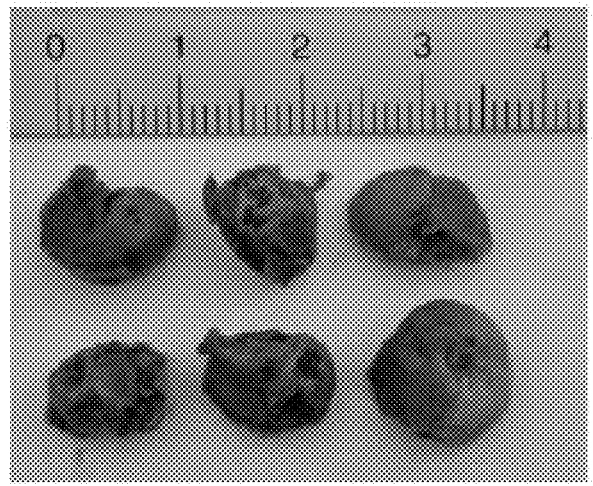
FIG. 8 shows the ectopic fresh bone of long chain rhBMP-2.

(2) In Vivo Evaluation 0.25 mg of the rhBMP-2 obtained was implanted to leg muscle of Kunming mouse. The results (FIG. 8) demonstrated that, the amount of ectopic bone formation increased compared to that formed in Example 4, indicating that the osteoinductivity of the rhBMP-2 obtained was better than that obtained in Example 4. In contrast, no new bon could be found in the control group (without rhBMP-2).

Example 6

For Comparison

Construction of Recombinant Bacteria Containing Long Chain hBMP-2 Genes and Preparation of rhBMP-2 (Without Optimization)

1. Long Chain hBMP-2 Genes

Based on the cDNA sequence of natural hBMP-2 mature peptide (SEQ ID NO: 1), the nucleotides (SEQ ID NO: 5, 1-48, AAA CGT CAT GAT GGC AAA GGC CAT CCG CTG CAT AAA CGC GAA AAA CGC) corresponding to 16 amino acide residues of natural hBMP-2 prepeptide (SEQ ID NO: 6, 1-16, Lys Arg His Asp Gly Lys Gly His Pro Leu His Lys Arg Glu Lys Arg) were added to the 5' terminal to obtain the long chain rhBMP-2 gene (SEQ ID NO: 5).

2. Construction of Recombinant Vectors

Restriction enzyme cleavage site and translation initiation nucleotide codon (GAATTCATG) were added to the 5' terminal of DNA sequence of optimal long chain hBMP-2 obtained in step 1 (SEQ ID NO: 8). The double stop codon and restriction enzyme cleavage site (TAGTAGGGATCC) were added to the 3' terminal. The gene was synthesized and inserted into vector pBV220 by digestion and ligation. The rhBMP-2 expressing plasmid was obtained, named pRB-hBMP-L-3. The inserted elements were confirmed by digestion and sequencing.

3. Construction, Verification and Storage of Engineered Bacteria

Competent *E. coli* cell (JM109) was prepared by the conventional method of calcium chloride. The competent *E. coli* was transformed by the expression vector obtained in step 2. From the LB plate with appropriate antibiotics, several positive colonies were picked and cultured overnight in LB. Plasmid DNA was isolated and analyzed by restriction enzyme digestion and sequencing to confirm the presence of the correct expression vector. Once the correct clone was identified, the colony was purified and inoculated into flasks containing LB culture medium with glucose and antibiotics, cultured for 15 hrs at 180 rpm and 30° C. in air bath shaker. Sterile glycerol was mixed with the culture to make a glycerol stock of the recombinant cell with the final glycerol concentration of 15%. The glycerol stock was transferred to a cryovial and stored at −80° C. freezer.

4. Culture of Engineered Bacteria

From the glycerol stock of the engineered bacteria, the original colony was streaked out for single colonies on an LB plate containing appropriate antibiotics, a single colony was isolated and inoculated into flasks containing LB culture medium containing 10 g/l tryptone, 5 g/l yeast extract, 5 g/l NaCl and 100 µg/mL penbrtin. After 8 hrs culture under the conditions of 180 rpm and 30° C. in air bath shaker, the culture was inoculated into LB culture medium with volume ratio of 1:10 for another 4 hrs under the condition of 180 rpm, 30° C. and pH 7.0±0.2. After that, temperature was raised to 42° C. to continue culture for 6 hrs. At the end of culture, medium was centrifuged at 7500 rpm, 4±2° C., and bacteria were collected and disrupted. The polyacrylamide gel electrophoresis (PAGE) was run to analyze the cell lysis. The result indicated that compared to the recombinant bacteria before induction and blank bacteria without plasmid, a clear band corresponding to molecular weight of the target protein (13 KD) was observed.

5. Extracting and Washing of Inclusion Bodies

The bacteria collected in step 4 was mixed with TE solution at the ratio of 1 g:10 ml, then lysozyme was added at the ratio of 1 g:1 mg. The bacteria were broken by cell disruption technique, centrifuged at 10000 rpm. The precipitate was collected and mixed with washing buffer at the ratio of 1 g:20 ml (precipitate: washing buffer). After 2 hrs stirring, the cell lysis was centrifuged and collected at 4±2° C., washed again with washing buffer. Then, 10 mM Tris (pH 7.5) solution was added at a ratio of 1 g precipitate:20 mL Tris, washed, and centrifuged to collect inclusion bodies.

6. Solubilization and Renaturation of Inclusion Bodies

Lysis solution comprising 6 M Gu-HCl, 20 mM PBS, 10 mM DTT was added at the ratio of 1 g:10 ml (inclusion bodies: lysis solution), stirred to dissolve inclusion body precipitate for 8 hrs at 4±2° C., centrifuged for 30 min at 10000 rpm and 4±2° C. The supernatant was collected, diluted to protein level of 0.1 mg/ml, then mixed with refolding solution to renature for 10 d. The refolding solution contained 20 mM $Na_2HPO_4.12H_2O$, 1.5 mM $NaH_2PO_4.2H_2O$, 140 mM NaCl, 5 mM EDTA and 1 mM glutathione.

7. Purification of Protein

Bioactive dimer of rhBMP-2 was recovered from refolding solution by conventional purification processes, such as anion-exchange chromatography, cation-exchange chromatography, and molecular-exclusion chromatography. And then the obtained rhBMP-2 was lyophilized at −30~7° C.

The results determined by non-reducing SDS-PAGE indicated that the protein purity was above 95% and the molecular weight was about 26 KD. HLPC analysis also showed that the purity was above 95%. Also, the amino acid sequences of N-terminus and C-terminus were the same as those deduced from the nucleotide sequences.

The average yield of rhBMP-2 was 6.3 mg/L.

8. Test of Bioactivity

The bioactivity of the BMP-2 was detected by in vitro cell culture and in vivo ectopic bone formation.

(1) In Vitro Cell Culture

C2C12 cells are plated into 96 well tissue culture plates at a density of $1.0\times10^4$ cells/mL in 100 µL of media (DMEM with 10% heat inactivated fetal calf serum, 100 u antibiotics. The cells are cultured at 37° C. in humidified atmosphere of 5% $CO_2$/95% air. After 3 days incubation, the culture media was removed and replaced with 200 µL DMEM medium containing rhBMP-2 dimer at the range from 1 µg/mL to 12 µg/mL. The equal volume DMEM media with rhBMP-2 monomer at the same concentration and without rhBMP-2 were used as control. Each concentration was conducted in triplicate. After 3 days, plates are removed from the 37° C. incubator and the test media are removed from the cells. The C2C12 cells were washed 2 times with PBS. Then, 50 µL 1% Nonidet P-40 solution (NP-40, constructed by ALP buffer solution) was added to each well at room temperature (RT) for 1 h to obtain cell lysate. After that, 50 µL of 1 mg/mL p-nitrophenylphosphate (Sangon, Shanghai, China) substrate solution (pH 9) was added and incubated for another 15 min at RT. The reaction was quenched by adding 100 µL, of 0.2 N NaOH, and the absorbance of ALP was quantified at the wavelength of 405 nm using a microplate reader (SPECTRAmax 384, Molecular Devices, USA). The results indicated that within the concentration from 1 µg/mL to 12 µg/mL, the rhBMP-2 produced showed lower ALP activity than that of the rhBMP-2 obtained in Example 4 and 5. But the rhBMP-2 monomer or without rhBMP-2 groups had no detectable ALP activity.

(2) In Vivo Evaluation 0.25 mg of the rhBMP-2 obtained was implanted to leg muscle of Kunming mouse. The results demonstrated that, the amount of ectopic bone formation decreased compared to that formed in Example 4 and 5, indicating that the osteoinductivity of the rhBMP-2 obtained was lower than that obtained in Example 4 and 5. In contrast, no new bon could be found in the control group (rhBMP-2 monomer).

Example 7

Comparation of the rhBMP-2 Productivity in Different Recombinant Cells Harboring Different Recombinant hBMP-2 Expression Vectors The construction of three kinds of rhBMP-2 expression vectors and the corresponding engineered bacteria, as well as the preparation of rhBMP-2 were showed in Examples 1-3.

The expression level of rhBMP-2 were analyzed and compared. The results indicated that, in recombinant cell harboring the rhBMP-2 gene (SEQ ID NO:4) optimized by software and further artificial optimization, the expressing level of rhBMP-2 was improved by about 50% when compared with the control (SEQ ID NO: 1). However, no significant difference was observed in the group with only software optimization (SEQ ID NO: 3), as showed in Table 1.

TABLE 1

Effect of nucleotide optimization on the expressing level of rhBMP-2

| Gene (SEQ ID NO:) | Batch | Cell concentration $OD_{A600}$ | The total protein of inclusion bodies | The production of rhBMP-2 | Source of origin |
|---|---|---|---|---|---|
| Further optimized SEQ ID NO: 4 | 20080521 | 3.1 | 145.0 mg | 30.5 mg | Example 2 |
| Optimized gene SEQ ID NO: 3 | 20080601 | 2.9 | 113.1 mg | 21.2 mg | Example 1 |
| original gene SEQ ID NO: 1 | 20080612 | 3.1 | 108.5 mg | 19.8 mg | Example 3 |

Example 8

Analysis of Renaturation Efficiency of the Long Chain rhBMP-2 and the Mature rhBMP-2

The preparation of rhBMP-2 mature peptide and long chain rhBMP-2 were shown in Examples 2 and 5, and the final yields were analyzed. Compared with 114 mature peptide of rhBMP-2, the long chain rhBMP-2 had higher yield renaturation efficiency and the yield of recombinant protein was improved by 34% (Table 2). This indicated that although both optimized genes (SEQ ID NO:4 and 8) could be to obtain high level of rhBMP-2 production, the SEQ ID NO:8 was superior considering the renaturation efficiency of the inclusion body.

TABLE 2

Analysis of the renaturation yield of mature peptide and long chain rhBMP-2

| | Batch | Total protein in renaturation solution | The yield of chromatographic column | Gross production of rhBMP-2 |
|---|---|---|---|---|
| Mature peptide hBMP-2 | 20080521 | 145.0 mg | 21% | 30.5 mg(Example 2) |
| Long chain rhBMP-2 | 20080628 | 147.8 mg | 27.2% | 40.2 mg(Example 5) |

Example 9

Optimization of hBMP-2 Mature Peptide, Construction of Recombinant Bacteria and Changing Conditions for Preparation of rhBMP-2

The steps of Example 2 were repeated with the exception of steps 5 and 6.

5. Extracting and Washing of Inclusion Bodies

The bacteria collected in step 4 was mixed with TE solution at the ratio of 1 g:15 ml, then lysozyme was added at the ratio of 1 g:3 mg. The bacteria were broken by cell disruption technique, centrifuged at 8000 rpm. The precipitate was collected, washed with 2× washing buffer at the ratio of 1 g:20 ml (precipitate: washing buffer). After 2 hrs stirring, the cell lysis was collected by centrifugation at 4±2° C., washed again with 2× washing buffer. Then, the cell lysis was washed with 10 mM Tris (pH 7.5) solution at a ratio of 1 g precipitate:20 mL Tris, precipitated by centrifugation to obtain inclusion bodies.

6. Solubilization and Renaturation of Inclusion Bodies

Lysis solution comprising 8 M Urea, 20 mM PBS, 10 mM DTT was added at the ratio of 1 g:17 ml (inclusion bodies: lysis solution), stirred to dissolve inclusion body precipitate for 8 h at 4±2° C., centrifuged for 30 min at 9000 rpm and 4±2° C. The supernatant was collected, diluted to protein level of 0.7 mg/ml, then mixed with refolding solution to renature for 20 d. The refolding solution contained 20 mM $Na_2HPO_4 \cdot 12H_2O$, 1.5 mM $NaH_2PO_4 \cdot 2H_2O$, 140 mM NaCl, 5 mM EDTA and 1 mM glutathione.

7. Purification of Protein

The results analyzed by non-reducing SDS-PAGE indicated that the protein purity was above 95% and the molecular weight was about 26 KD. HLPC analysis also showed that the purity was above 95%. Also, the sequences of N-terminus and C-terminus were the same as those deduced from the nucleotide sequences.

The average yield of rhBMP-2 was 6.98 mg/L.

Example 10

Alternative Optimized Sequences Based on SEQ ID NO: 4

Follow the procedures similar to Example 2, except that the sequence of SEQ ID NO: 4 was partially replaced by the following sequence:

The codon for $23^{th}$ amino acid ttc was changed to ttt and the codon for $86^{th}$ amino acid aag was changed to aaa, the optimized nucleotide sequence still encoded the rhBMP-2 mature peptide as showed in SEQ ID NO:2.

The results determined by non-reducing SDS-PAGE indicated that the protein purity was above 95% and the molecular weight was about 26 KD. HLPC analysis also showed that the purity was above 95%. Also, the amino acid sequences of N-terminus and C-terminus were the same as those deduced from the nucleotide sequences.

The average yield of rhBMP-2 was 6.04 mg/L.

All the documents cited herein are incorporated into the invention as reference, as if each of them is individually incorporated. Further, it would be appreciated that, after reading the above illustration of the invention, the expert in the related field could make certain changes or modifications to the invention, and these equivalents would still be within the scope of the invention defined by the appended claims of the present application.

REFERENCES

[1] Baneyx F. Recombinant protein expression in *Escherichia coli*[J], Curr Opin Biotechnol, 1999, 10:411-421.

[2] Wu G, Bashir-Bello N, Freeland S J. The synthetic gene designer: a flexible web platform to explore sequence manipulation for heterogonous expression[J]. Protein Expr Purif, 2006, 47(2):441-445.

[3] Kane J F. Effects of rare condon clusters on high-level expression of heterologus proteins in *E. coli*. Curr Opin Biotechol, 1995, 6:494-500

[4] Henaut A, Danchin A. Analysis and Predictions from *Escherichia coli* Sequences in: *Escherichia coli* and *Salmonella*[M]. Washington D.C.: ASM press, 1996.

[5] Sorensen M A, Kurland C G, Pedersen S, et al. Codon usage determines translation rate in *Escherichia coli*[J]. Journal of Molecular Biology, 1989, 207(2):365-377.

[6] Zhang S P, Zubay G, Goldman E, et al. Low-usage codons in *Escherichia coli*, yeast, fruit fly and primates [J]. Gene, 1991, 105(1):61-72.

[7] Comeron J M, Aguade M. An evaluation of measures of synonymous codon usage bias [J]. Journal of Molecular Evolution, 1998, 47(3):268-274.

[8] Xu L, Li T, Zhou X W, Huang P T. Design and Implementation of DB Sequence Optimization Software [J]. Chinese Journal of Biotechnology, 2006, 22(6):1032-1035.

What is claimed is:

1. An isolated polynucleotide encoding recombinant human bone morphogenetic protein-2 (rhBMP-2), wherein the polynucleotide encodes the mature polypeptide of rhBMP-2 as set forth in SEQ ID NO: 2, and the polynucleotide has the following properties:
   in SEQ ID NO: 2, the codon of the 9$^{th}$ amino acid is cgc;
   in SEQ ID NO: 2, the codon of the 23$^{th}$ amino acid is ttt;
   in SEQ ID NO: 2, the codon of the 34$^{th}$ amino acid is gcg;
   in SEQ ID NO: 2, the codon of the 86$^{th}$ amino acid is aaa; and
   in SEQ ID NO: 2, the codon of the 110$^{th}$ amino acid is ggc.

2. The polynucleotide of claim 1 wherein the expression level of rhBMP-2 of the polynucleotide in *Escherichia coli* is improved by at least 40%, or at least 50% in *Escherichia coli*, as compared with the polynucleotide as set forth in SEQ ID NO: 1.

3. The polynucleotide of claim 1 wherein the polynucleotide sequence is as set forth in SEQ ID NO: 4.

4. The polynucleotide of claim 1 wherein the polynucleotide sequence is as set forth in SEQ ID NO: 8.

5. An expression vector for rhBMP-2 preparation wherein the expression vector contains the polynucleotide of claim 1.

6. An engineered cell for rhBMP-2 preparation wherein the engineered cell comprises the expression vector of claim 5.

7. The engineered cell of claim 6 wherein the engineered cell is *Escherichia coli*.

8. A method for the preparation of rhBMP-2 comprising the following steps:
   (a) culturing the engineered cell of claim 6 under suitable expression conditions thereby secreting the rhBMP-2, wherein the engineered cell is *Escherichia coli*;
   (b) separating the expressed rhBMP-2; and
   (c) purifying the expressed rhBMP-2.

9. The method of claim 8 wherein the step (b) further comprises:
   (i) denaturing of the inclusion bodies of rhBMP-2;
   (ii) renaturing of rhBMP-2 protein; and
   (iii) purifying the renatured rhBMP-2.

* * * * *